US011615890B2

(12) United States Patent
Chang et al.

(10) Patent No.: US 11,615,890 B2
(45) Date of Patent: Mar. 28, 2023

(54) METHOD AND SYSTEM FOR THE COMPUTER-ASSISTED IMPLEMENTATION OF RADIOLOGY RECOMMENDATIONS

(71) Applicant: RAD AI, Inc., Berkeley, CA (US)

(72) Inventors: Jeffrey Chang, Berkeley, CA (US); Doktor Gurson, Berkeley, CA (US); Scott Whitney, Berkeley, CA (US); Joseph Zachary Allen, Berkeley, CA (US); Shokoufeh Kazemlou, Berkeley, CA (US); Maxwell Taylor, Berkeley, CA (US); Craig Warner, Berkeley, CA (US); Eric Purdy, Berkeley, CA (US)

(73) Assignee: RAD AI, INC., Berkeley, CA (US)

( * ) Notice: Subject to any disclaimer, the term of this patent is extended or adjusted under 35 U.S.C. 154(b) by 0 days.

(21) Appl. No.: 17/690,751

(22) Filed: Mar. 9, 2022

(65) Prior Publication Data

US 2022/0293271 A1   Sep. 15, 2022

Related U.S. Application Data

(60) Provisional application No. 63/158,706, filed on Mar. 9, 2021.

(51) Int. Cl.
*G16H 50/20* (2018.01)
*G16H 15/00* (2018.01)
(Continued)

(52) U.S. Cl.
CPC ............. *G16H 50/20* (2018.01); *G16H 10/60* (2018.01); *G16H 15/00* (2018.01); *G16H 40/20* (2018.01); *G16H 50/30* (2018.01); *G16H 70/20* (2018.01)

(58) Field of Classification Search
CPC ........ G16H 50/20; G16H 40/20; G16H 10/60; G16H 15/00; G16H 50/30; G16H 70/20
(Continued)

(56) References Cited

U.S. PATENT DOCUMENTS 10,127,662 B1   11/2018   Reicher et al.
10,140,421 B1   11/2018   Bernard et al.
(Continued)

FOREIGN PATENT DOCUMENTS

| CN | 111414464 A | 7/2020 |
| WO | 0239415 A2 | 5/2002 |
| WO | 2019025601 A1 | 2/2019 |

OTHER PUBLICATIONS

Lou, R., Lalevic, D., Chambers, C., Zafar, H. M., & Cook, T. S. (2020). Automated detection of radiology reports that require follow-up imaging using natural language processing feature engineering and machine learning classification. Journal of digital imaging, 33(1), 131-136. (Year: 2020).*

Dai, Ning, et al., "Style transformer: Unpaired text style transfer without disentangled latent representation", Ithaca: Cornell University Library, arXiv.org. (Year: 2019).
(Continued)

*Primary Examiner* — Joshua B Blanchette
*Assistant Examiner* — Winston Furtado
(74) *Attorney, Agent, or Firm* — Jeffrey Schox; Caitlin Ploch

(57) ABSTRACT

A method for the computer-assisted implementation of radiology recommendations includes any or all of: receiving a set of inputs; determining and/or identifying a set of findings; determining a set of follow-up recommendations; and triggering a set of outputs and/or actions based on the set of follow-up recommendations. A system for the computer-assisted implementation of radiology recommendations preferably includes and/or interfaces a set of computing subsystems and/or processing subsystems, but can addition-
(Continued)

ally include and/or interface with a set of devices (e.g., user devices), models, and/or any other components.

17 Claims, 14 Drawing Sheets

(51) Int. Cl.
    *G16H 10/60*     (2018.01)
    *G16H 50/30*     (2018.01)
    *G16H 70/20*     (2018.01)
    *G16H 40/20*     (2018.01)

(58) Field of Classification Search
    USPC .......................................................... 705/3
    See application file for complete search history.

(56) References Cited

U.S. PATENT DOCUMENTS

| | | | |
|---|---|---|---|
| 2013/0290031 | A1 | 10/2013 | Kay et al. |
| 2014/0379378 | A1 | 12/2014 | Cohen-Solal et al. |
| 2015/0112725 | A1* | 4/2015 | Ryan ................ G06F 16/285 705/3 |
| 2015/0348229 | A1 | 12/2015 | Aguirre-Valencia et al. |
| 2018/0060533 | A1 | 3/2018 | Reicher et al. |
| 2018/0330828 | A1 | 11/2018 | Hayter |
| 2019/0021677 | A1 | 1/2019 | Grbic et al. |
| 2019/0122073 | A1 | 4/2019 | Ozdemir et al. |
| 2019/0139218 | A1 | 5/2019 | Song et al. |
| 2020/0334416 | A1* | 10/2020 | Vianu .................... G06N 7/005 |
| 2020/0342967 | A1 | 10/2020 | Bronkalla et al. |
| 2021/0090694 | A1* | 3/2021 | Colley .................... G16B 40/00 |
| 2021/0110912 | A1* | 4/2021 | Mukherjee ............. G06N 5/046 |
| 2021/0327596 | A1* | 10/2021 | Tahmasebi Maraghoosh ............. G16H 20/00 |

OTHER PUBLICATIONS

Ebesu, Travis Akira, "Deep learning for recommender systems", (Order No. 13900137). Available from ProQuest Dissertations & Theses Global. (2293976827). (Year: 2019).

Garud, Hrishkesh Deepak, et al., "Transforming human pose forecasting", (Order No. 27814956). Available from ProQuest Dissertations & Theses Global. (2399247743). (Year: 2019).

Jettaku, Amarin, et al., "Relation extraction between bacteria and biotopes from biomedical texts with X attention mechanisms and domain-specific contextual representations", BMC Bioinformatics, 20, 1-17, (2019).

Koncel-Kedziorski, Rik, et al., "Understanding and generating multi-sentence texts", (Order No. 13814316). Available from ProQuest Dissertations & Theses Global. (2305944561). (Year: 2019).

Nandhakumar, Nidhin, et al., "Clinically Significant Information Extraction from Radiology Report", DocEng '17: Proceedings of the 2017 ACM Symposium on Document Engineering, Aug. 2017, pp. 153-162.

Sanjabi, Nima, "Abstractive text summarization with attention-based mechanism", (Projecte Final de Master Oficial). UPC, Facultat d'Informatica de Barcelona. (Year: 2018).

Song, Huan, "Data-driven representation learning in multimodal feature fusion", (Order No. 10838232). Available from ProQuest Dissertations & Theses Global. (2094858110). (Year: 2018).

Xue, Y., et al., "Multimodal Recurrent Model with Attention for Automated Radiology Report Generation", Medical Image Computing and Computer Assisted Intervention—MICCAI 2018. MICCAI 2018. Lecture Notes in Computer Science, vol. 11070. Springer, Cham. https://doi.org/10.1007/978-3-030-00928-1_52 (Year: 2018).

Zech, John, et al., "Natural Language-based Machine Learning Models for the Annotation of Clinical Radiology Reports", Radiology Reports. Jan. 30, 2018 (Jan. 30, 2018).

Zhang, Yuhao, et al., "Learning to Summarize Radiology Findings", Oct. 8, 2018 (Oct. 8, 2018). 1-20 [retrieved on Nov. 18, 2020].

* cited by examiner

FIGURE 7A

Interface of worklist depicting progress of actions and/or outputs in a patient's follow-up

FIGURE 7C

Example of customization options (e.g., for radiology group, manager, PCP, etc.) associated with the types and/or triggers for actions/outputs

METHOD AND SYSTEM FOR THE COMPUTER-ASSISTED IMPLEMENTATION OF RADIOLOGY RECOMMENDATIONS

CROSS-REFERENCE TO RELATED APPLICATIONS

This application claims the benefit of U.S. Provisional Application No. 63/158,706, filed 9 Mar. 2021, which is incorporated in its entirety by this reference.

TECHNICAL FIELD

This invention relates generally to the radiology field, and more specifically to a new and useful system and method for computer-assisted implementation of radiology recommendations in the radiology field.

BACKGROUND

In current radiology workflows, one of the radiologist's main responsibilities is to identify, record, and make recommendations on his or her findings from the study (e.g., imaging, exam, etc.) in the radiology report. During this, the radiologist is typically most concerned with standard findings (equivalently referred to herein as critical findings), which refer to findings associated with the original intent of the study. However, oftentimes, there are other findings—incidental findings—which are not the original intent of the study, but could have (e.g., according to consensus guidelines, according to best practices, etc.) associated follow-up procedures (e.g., follow-up imaging, follow-up procedures, monitoring, etc.).

The reliability and consistency with which radiologists include follow-up recommendations for incidental findings in the report is highly variable among radiologists and even for individual radiologists. As such, it has been found that less than half (e.g., ~40%) of studies with significant incidental findings include specific recommendations for follow-up, and in only a small percentage (e.g., ~25%) of those cases is the follow-up actually performed.

To further compound the unreliability of addressing incidental findings, even when the incidental findings are noted in the report, the actual follow-up is poor, which can lead to any or all of: a missed opportunity for revenue (e.g., lack of follow-up imaging, lack of follow-up procedures associated with incidental findings, etc.) for the healthcare facility and/or radiology group, increased liability (e.g., for missing incidental findings, for missing follow-up, etc.) for the healthcare facility and/or radiology group, harm (e.g., illness, death, etc.) to the patient, or any number of other negative outcomes.

Thus, there is a need in the radiology field to create an improved and useful system and method for identifying, tracking, and following up with radiology findings and their associated recommendations.

BRIEF DESCRIPTION OF THE FIGURES

FIGS. 7A-7E depict specific examples of the determination, triggering, and management of a set of actions and/or outputs associated with follow-up recommendations for a set of patients.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
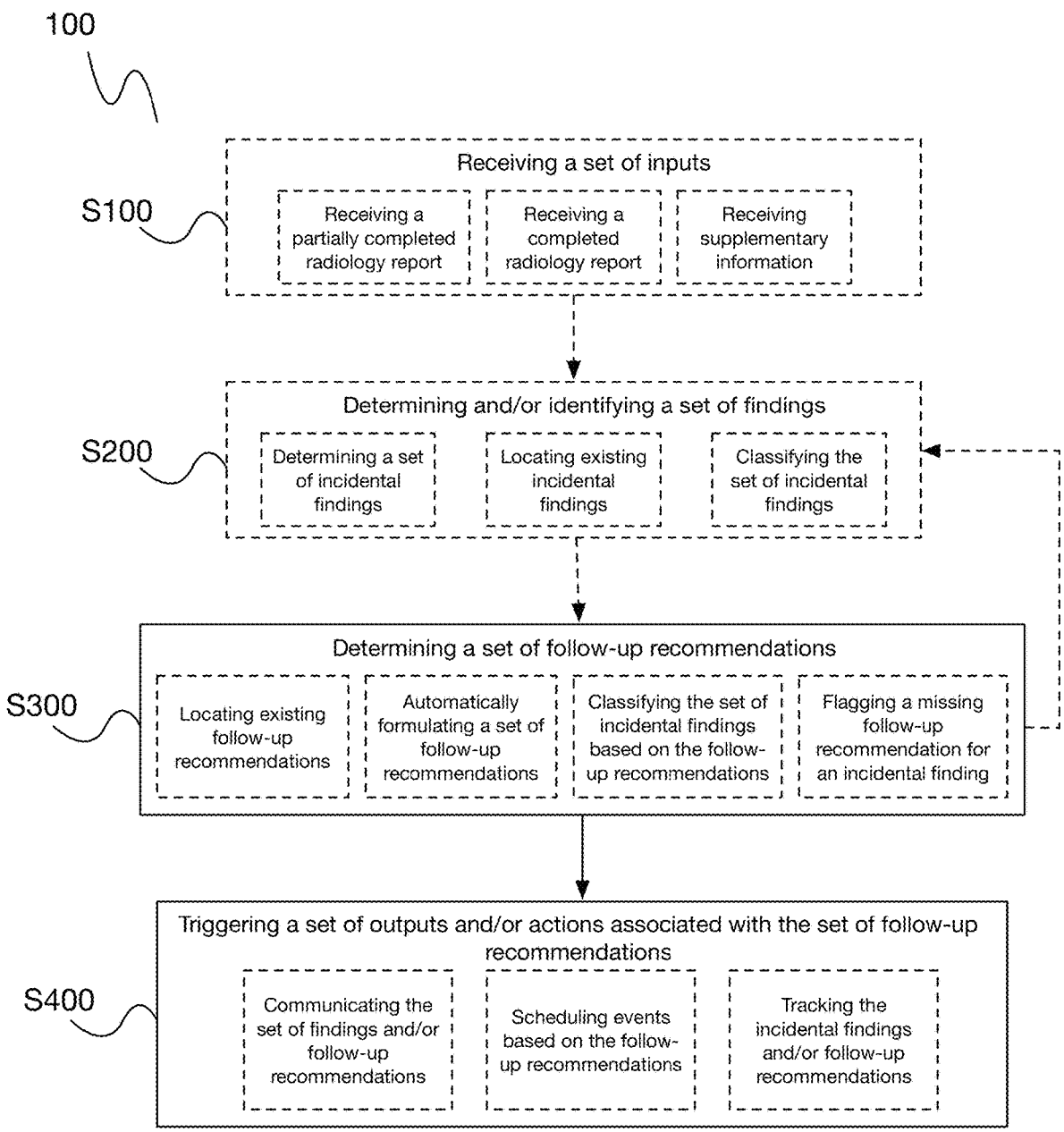
FIG. 1 is a schematic of a method for identifying and tracking radiology findings.
Figure 2A:
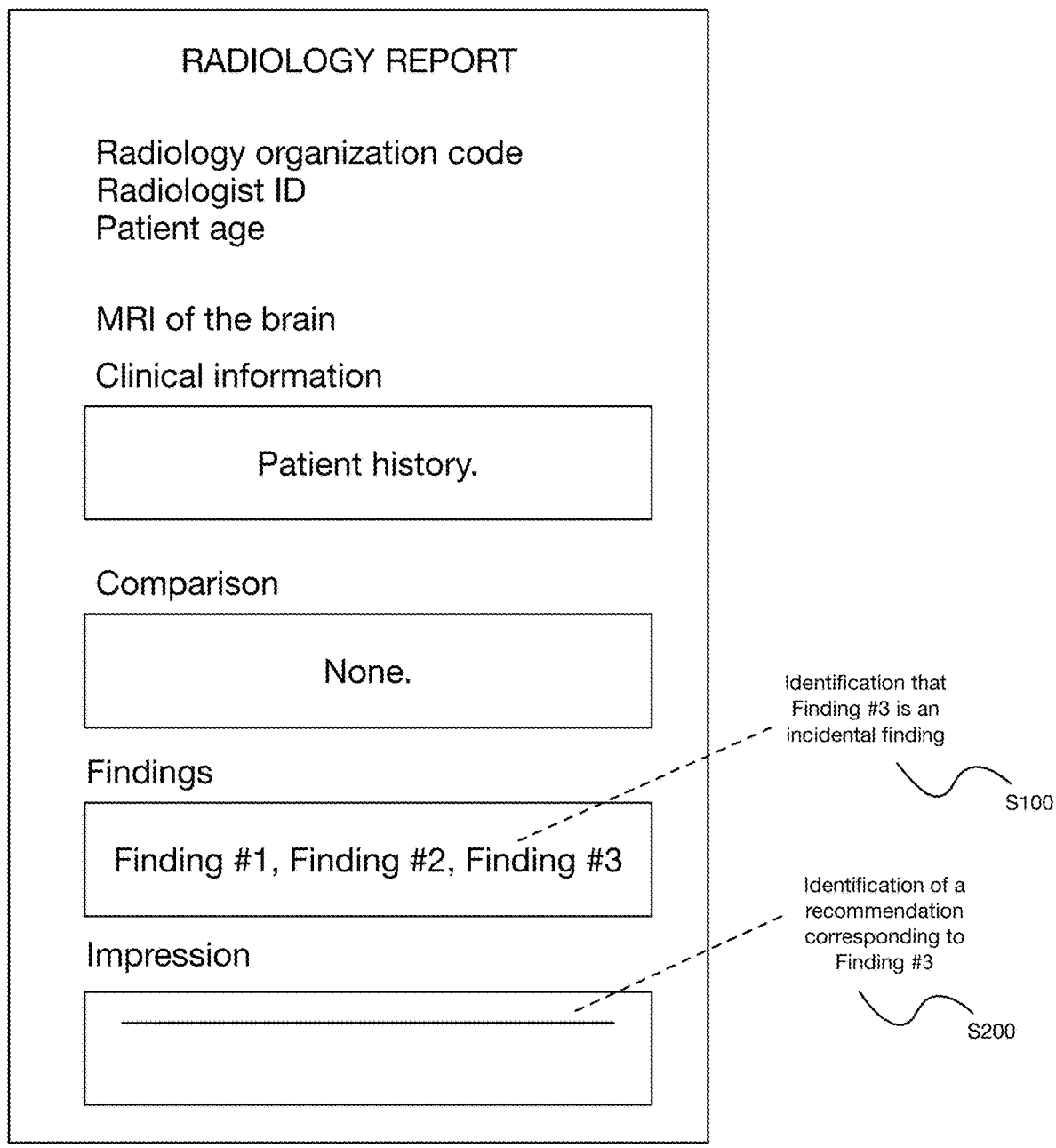
FIGS. 2A-2D depict variations of radiology reports and associated prompts related to the method 100.
Figure 2B:
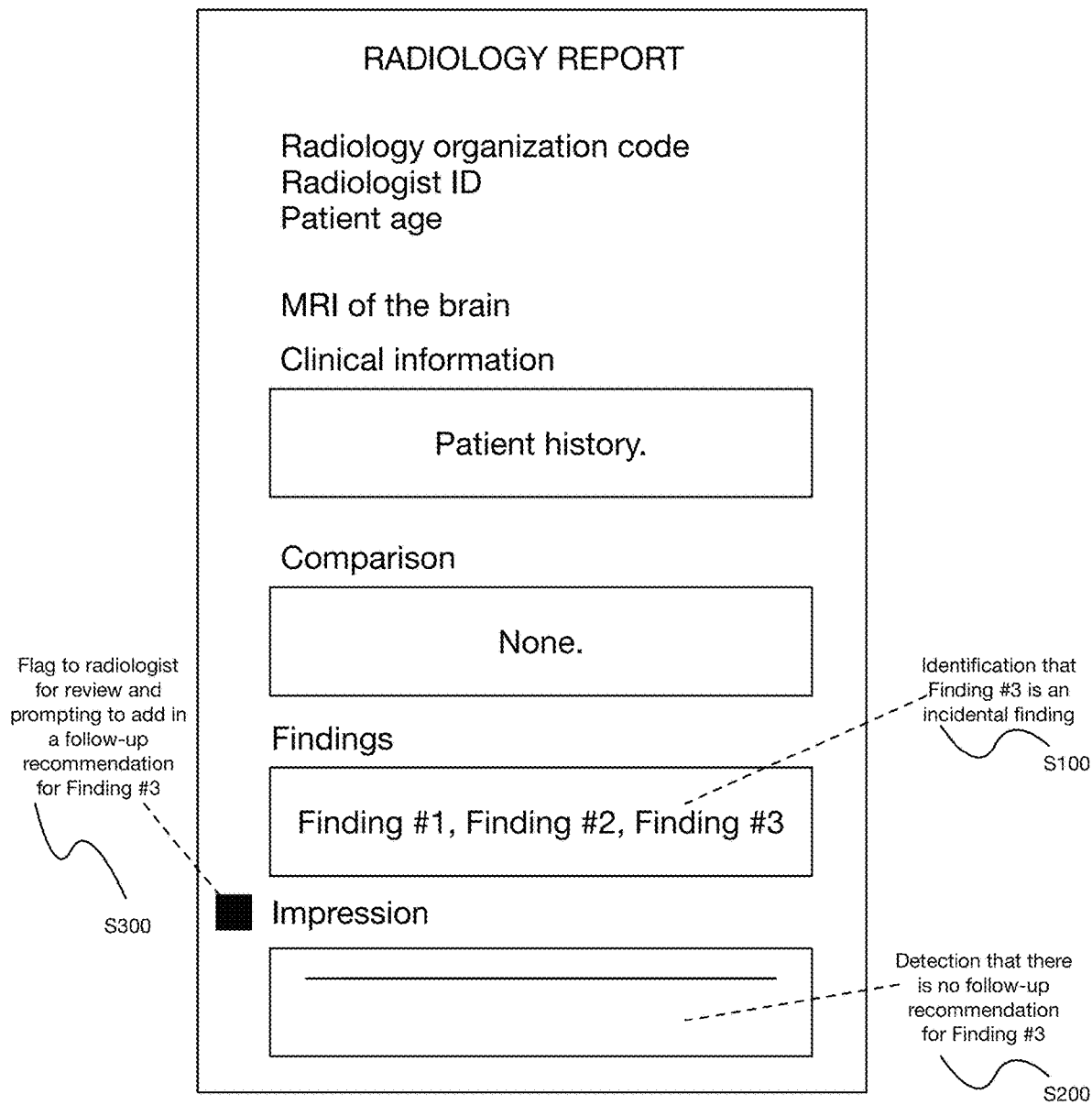
Figure 2C:
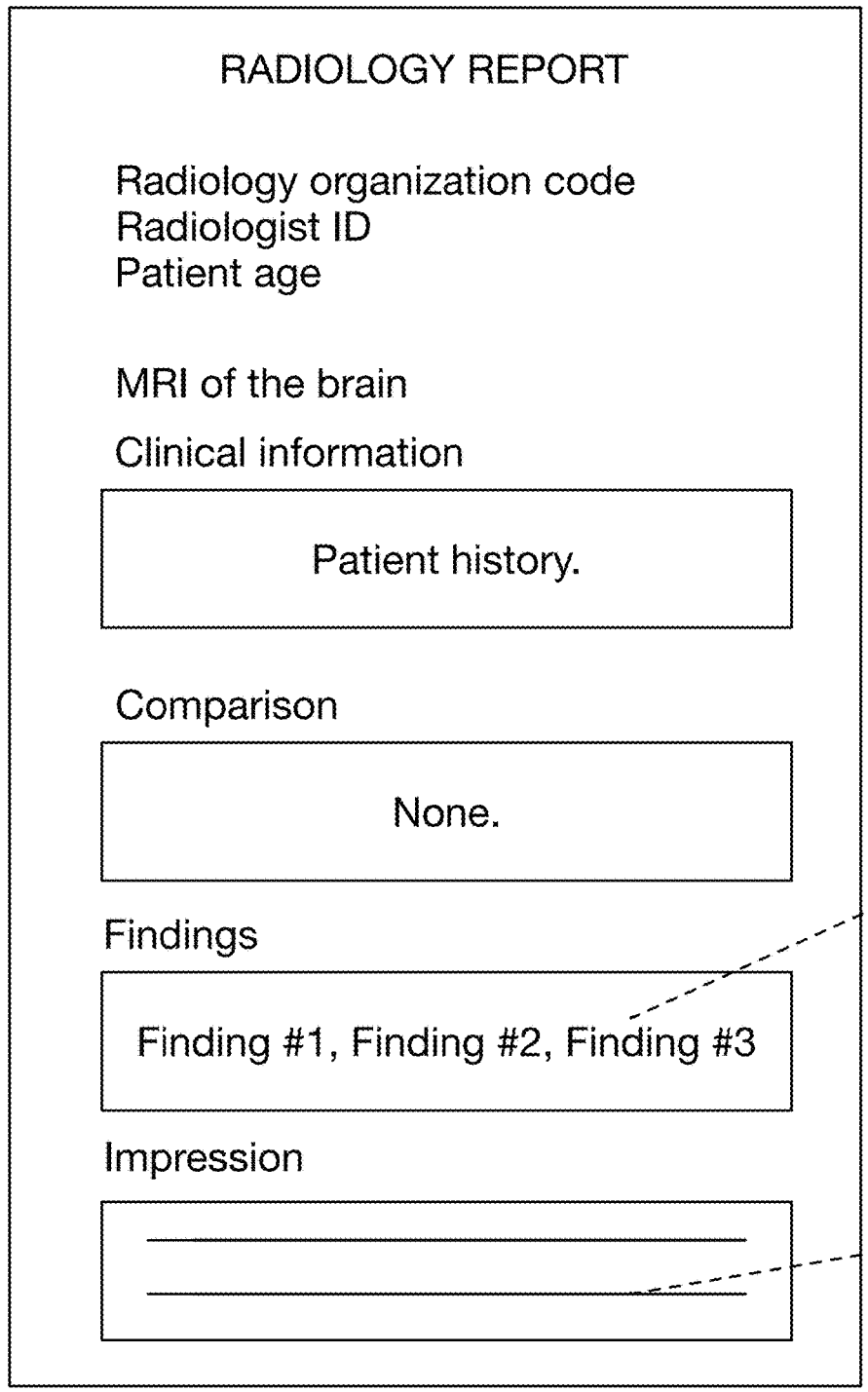
Figure 2D:
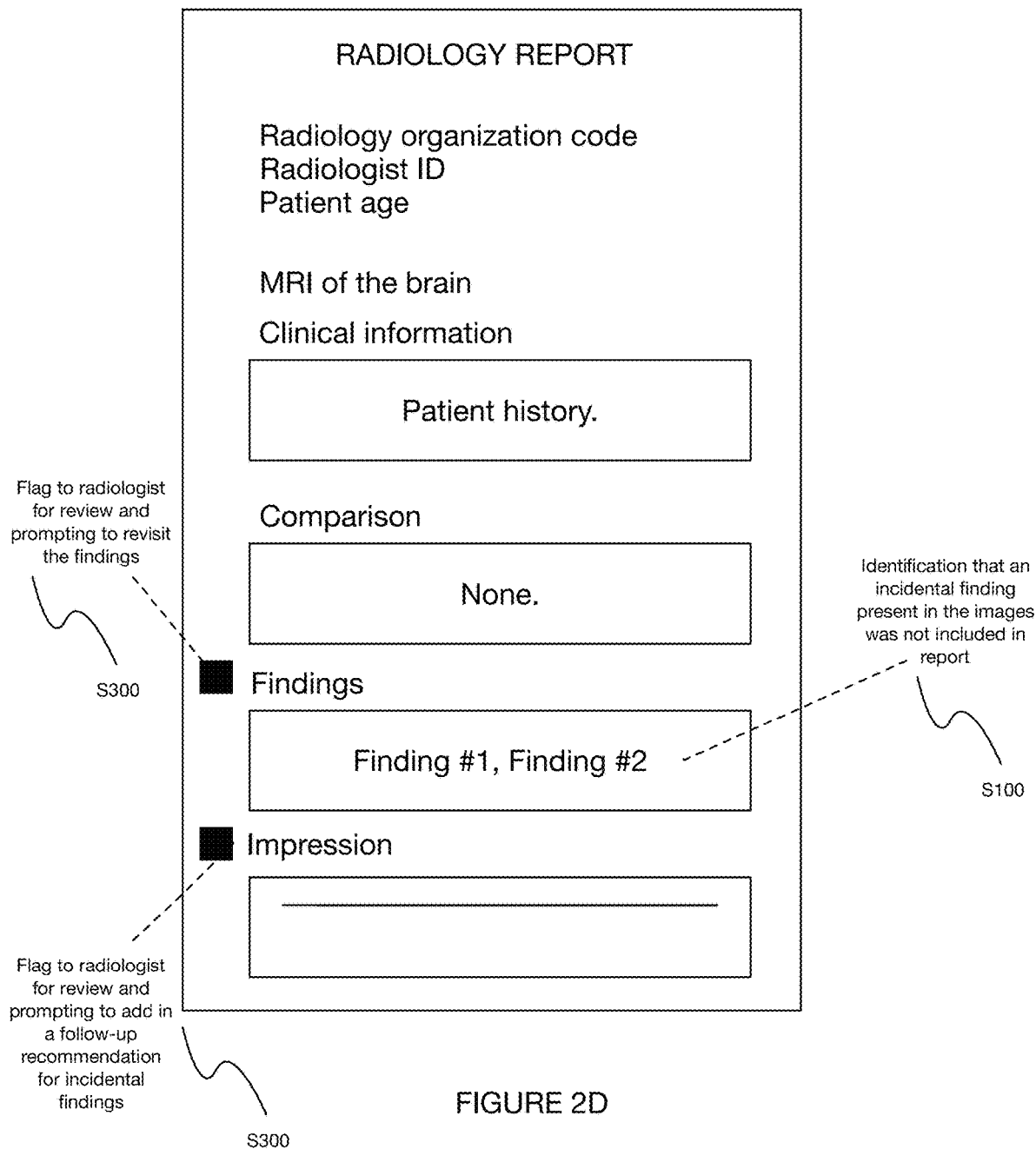

As shown in FIG. 1, a method 100 for the computer-assisted implementation of radiology recommendations includes any or all of: receiving a set of inputs S100; determining and/or identifying a set of findings S200; determining a set of follow-up recommendations S300; and triggering a set of outputs and/or actions based on the set of follow-up recommendations S400. Additionally or alternatively, the method 100 can include any or all of the methods, processes, embodiments, and/or examples described in any or all of: U.S. application Ser. No. 16/688,623, filed 19 Nov. 2019, and U.S. application Ser. No. 17/020,593, filed 14 Sep. 2020, each of which is incorporated in its entirety by this reference, or any other suitable processes performed in any suitable order.

The method 100 is preferably performed with a system 200 as described below, but can additionally or alternatively be performed with any suitable system(s), such as, but not limited to, any or all of systems, components, embodiments, and/or examples described in any or all of the applications referenced and incorporated above.

Figure 6:
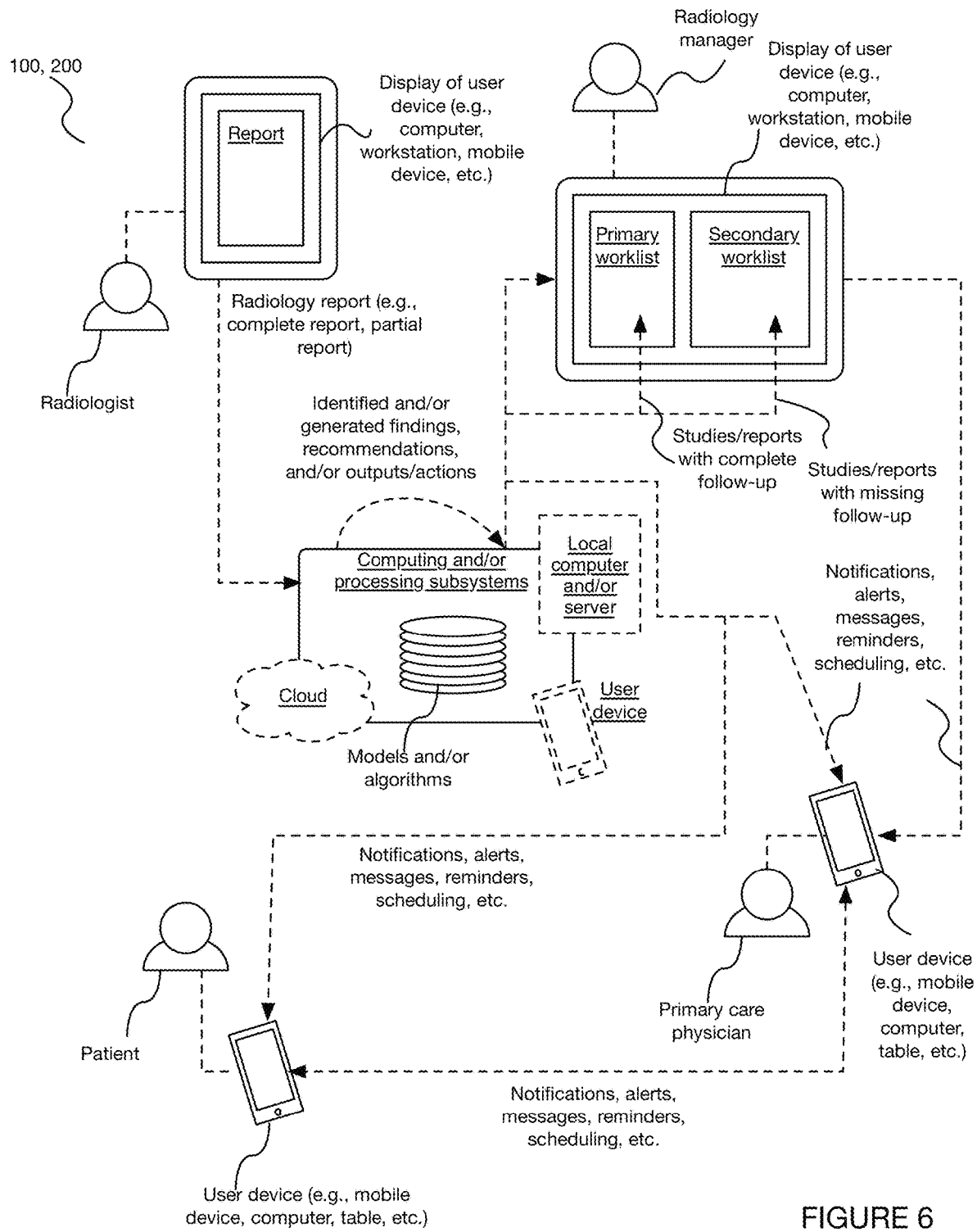
FIG. 6 depicts a variation of a system for identifying and tracking radiology findings, along with information flows involved in a variation of a method for identifying and tracking radiology findings.

As shown in FIG. 6, a system 200 for the computer-assisted implementation of radiology recommendations preferably includes and/or interfaces a set of computing subsystems and/or processing subsystems, but can additionally include and/or interface with a set of devices (e.g., user devices), models, and/or any other components. Additionally or alternatively, the system 200 can include and/or interface with any or all of the systems, components, embodiments, and/or examples as described in U.S. application Ser. No. 16/688,623, filed 19 Nov. 2019, and/or U.S. application Ser. No. 17/020,593, filed 14 Sep. 2020, each of which is incorporated in its entirety by this reference.

2. Benefits

The method and system for automatically identifying and tracking radiology findings can confer several benefits over current systems and methods.

In a first variation, the method and/or system confer the benefit of ensuring that incidental findings are present in a radiology report and/or that appropriate follow-up (e.g., according to the radiologist, according to the patient's clinicians, according to national consensus guidelines, etc.) for the incidental findings is included and adhered to, which can in turn confer numerous benefits in promoting preventative care. In specific examples, adhering to follow-up can include any or all of: ensuring that appropriate follow-up is communicated to the clinician(s) (e.g., patient's primary care physician) who will ultimately be responsible for ordering the follow-up study or consultation and/or for caring for the patient long-term as an outpatient; ensuring that the appropriate follow-up is communicated clearly to the patient, so that the patient understands the follow-up and its potential impact on the patient's long-term health; ensuring that appropriate follow-up is performed according to a particular (e.g., recommended) timeline; reducing liability of physicians (e.g., primary care physicians, ER doctors, radiologists, etc.) and/or radiology groups and/or healthcare facilities which results from not properly communicating and/or enforcing follow-up recommendations; reducing costs in the health care system associated with the delayed response to and/or lack of response to detected incidental findings; facilitating the matching of a patient with a PCP (e.g., in an event that the patient does not have a PCP); and/or adhering to follow-up recommendations in any other way(s).

In a second variation, additional or alternative to the first, the method confers the benefit of triggering an action in response to follow-up recommendations associated with the incidental findings, which can function to ensure that the follow-up recommendations are performed (e.g., immediately, over a significant time period, during a change in clinician associated with the patient, etc.). In specific examples, the triggered actions can include any or all of: pulling another physician (e.g., emergency room [ER] physician, patient's primary care physician, on-call physician, etc.) into the loop (e.g., notifying the physician, assigning the physician to the patient, etc.); establishing communication between individuals and/or entities (e.g., between an ER physician and a primary care physician, between the patient and a physician, etc.); setting automated reminders; automatically scheduling actions (e.g., lab work, imaging, examinations, specialist appointments, etc.) associated with the follow-up recommendations; facilitating the matching of a patient with a primary care physician (PCP) in an event that the patient does not have a PCP; and/or any other actions.

In a third variation, additional or alternative to those described above, the method confers the benefit of automatically determining any or all of the incidental findings, automatically determining and/or generating any or all of the associated follow-up recommendations for the incidental findings, and/or partially or fully automating any or all of the processes of the method. In specific examples, a set of trained models (e.g., machine learning models, deep learning models, etc.) can be used for any or all of: automatically determining a set of findings (e.g., incidental findings); automatically creating and/or filling in any or all of the radiology report; automatically triggering actions; and/or any other suitable processes.

In a set of specific examples, any or all of the method is performed in absence of input from a radiologist or other user, which can be equivalently referred to herein as a "zero-click" process.

In a fourth variation, additional or alternative to those described above, the system and/or method confer the benefit of establishing uniformity (e.g., a set of uniform processes, guidelines, etc.) in detecting, determining, and/or responding to follow-up recommendations associated with incidental findings (e.g., significant incidental findings). In a set of specific examples In a fifth variation, additional or alternative to those described above, the system and/or method confer the benefit of detecting and/or locating information within various different types, formats, and/or organizational styles of radiology reports or any other documents. In a set of specific examples, a set of trained models is used to locate incidental findings and/or follow-up recommendations within a radiology report (e.g., from an unspecified section in a radiology report). Additionally, a set of rule-based logic can optionally be used in combination with the trained models.

Additionally or alternatively, the system and method can confer any other benefit.

3. System

As shown in FIG. 6, a system 200 for the computer-assisted implementation of radiology recommendations preferably includes and/or interfaces a set of computing subsystems and/or processing subsystems, but can additionally include and/or interface with a set of devices (e.g., user devices), models, and/or any other components. Additionally or alternatively, the system 200 can include and/or interface with any or all of the systems, components, embodiments, and/or examples as described in U.S. application Ser. No. 16/688,623, filed 19 Nov. 2019, and/or U.S. application Ser. No. 17/020,593, filed 14 Sep. 2020, each of which is incorporated in its entirety by this reference.

The system 200 preferably functions to perform and/or enable performance of any or all of the processes of the method 100 (e.g., as described below), and further preferably functions to enable and/or facilitate the tracking and performance of follow-up recommendations associated with any or all of findings (e.g., incidental findings, significant incidental findings, primary findings, abnormal findings, etc.). In a set of specific examples, the system 200 functions to enable and/or facilitate the tracking and performance of follow-up recommendations for significant incidental findings associated with a patient.

The system 200 preferably includes and/or interfaces with a set of computing and/or processing subsystems, which can function to perform any or all of the processes of the method 100 described below and/or any other processes. Additionally or alternatively, the set of computing and/or processing subsystems can function to host (e.g., store, implement, execute, etc.) any or all of: a set of trained models (e.g., machine learning models, deep learning models, neural networks, etc.) and/or algorithms; rule-based logic; a set of decision trees; a set of lookup tables and/or databases (e.g., historical data associated with a patient, historical data for multiple patients, training data, etc.); and/or any other information. Further additionally or alternatively, the set of computing and/or processing subsystems can function to train and/or update one or more models, pre-process information, post-process information, and/or perform any other suitable functions.

The computing and/or processing subsystem can include and/or interface with any or all of: a set of computing devices (e.g., computers); a set of processing devices (e.g., processors, microprocessors, CPUs, GPUs, etc.); storage; memory; software programs/tools (e.g., radiology software, a speech recognition platform, etc.); a set of servers; and/or any other suitable components.

The computing and/or processing subsystem is preferably at least partially arranged remotely, but can additionally or alternatively be arranged locally (e.g., at a healthcare facility, at a radiologist's workstation, etc.), at a device (e.g., mobile device, stationary device, etc.) and/or among multiple devices, and/or at any suitable locations.

In a first variation, a set of trained models and/or rule-based logic are processed at a remote computing subsystem (e.g., cloud-based computing subsystem, remote server, etc.) which interfaces with a radiology platform (e.g., as described below), where the computing subsystem receives one or more of a set of inputs from the radiology platform (e.g., radiology report) for processing (e.g., to determine a set of findings, to determine a set of follow-up recommendations, etc.) in the method 100.

The system 200 can optionally include and/or interface with a set of models, which individually and/or collectively function to perform any or all of: detecting a set of findings; generating a set of findings; detecting a set of follow-up recommendations; generating a set of follow-up recommendations; determining and/or triggering a set of actions or outputs associated with the findings and/or follow-up recommendations; classifying any or all of the set of findings; inserting information (e.g., findings, recommendations, etc.) into a radiology report (e.g., at an optimal location, in a writing style of the radiologist, etc.). Additionally or alternatively, the set of models can function to perform any or all of: decreasing a processing time and/or improving one or more processing parameters (e.g., increasing accuracy, increasing radiologist approval/satisfaction, increasing readability and/or interpretability of a generated field, etc.); increasing a quality or consistency of follow-up recommendations; decrease the time for a radiologist to generate a report; decrease and/or eliminate actions (e.g., clicks, interventions in the report, etc.) for the radiologist; and/or performing any other suitable function(s).

The set of models are preferably located at (e.g., stored at, processed at, etc.) a computing subsystem (e.g., as described above), further preferably a remote computing subsystem (e.g., cloud computing system, remote server, etc.), but can additionally or alternatively be located at any or all of: a local computing subsystem, a combination of computing subsystems, and/or at any other suitable location(s).

The set of models preferably includes one or more machine learning models, further preferably one or more deep learning models. Additionally or alternatively, the set of models can include and/or interface with any or all of: algorithms, equations, rules and/or rulesets (e.g., rule-based and/or programmed logic), databases, lookup tables, decision trees, and/or any other suitable tools for generating, checking, editing, and/or otherwise processing language information in a radiology report.

The set of models can be configured to receive any number of inputs, such as, but not limited to, any or all of: a radiology report and/or any subset of a radiology report; a set of preferences; patient information (e.g., from the radiology report, from outside of the radiology report, from a historical radiology report, etc.); healthcare facility information; database information (e.g., from an EHR database, from an EMR database, from a PACS database, from a RIS database, etc.); radiology group information; radiology standards; billing procedures and/or guidelines; information from a database, storage, server, and/or software tools (e.g., EMR database, EHR database, RIS, CIS, PACS, etc.); a set of images (e.g., diagnostic images of the patient); video; and/or any other information from any suitable sources.

The set of models preferably includes one or more neural networks (e.g., feedforward neural networks, recurrent neural networks, convolutional neural networks, etc.), but can additionally or alternatively include any suitable algorithms (e.g., machine learning algorithms), decision trees, models, and/or any other suitable processing tools. The models can be trained through supervised learning (e.g., based on annotated reports, based on manually generated reports, based on synthesized reports, etc.), trained through unsupervised learning, untrained, or otherwise determined.

The set of models further preferably includes one or more deep learning models configured for natural language processing (NLP), such as one or more deep learning models with attention mechanisms, such as any or all of: a sequence-to-sequence architecture; one or more attention layers (e.g., in one or more encoders, in one or more decoders, etc.); one or more self-attention layers (e.g., in one or more encoders, in one or more decoders, etc.); and/or any other tools, features, and/or architecture. Additionally or alternatively, the deep learning model(s) can be configured for any suitable applications and/or otherwise designed.

The set of models preferably includes models implementing parallelization (e.g., processing all tokens at the same time) wherein processing data in order is not required, which can function to reduce training times and processing times. In preferred variations, for instance, the set of models includes a set of one or more transformers. In specific examples, for instance, the set of models includes a transformer model (equivalently referred to herein as a multi-transformer model) with one or more decoders that each consult a set of multiple encoders (e.g., in a sequential fashion, in a parallel fashion, etc.). Additionally or alternatively, the set of models can include any other suitable transformers and/or transformer systems (e.g., Bidirectional Encoder Representations from Transformers [BERT], Generative Pre-Trained Transformer [GPT], etc.); a transformer with any suitable number and/or arrangement of encoders and decoders (e.g., equal number of encoders and decoders, more encoders than decoders, more decoders than encoders, each decoder consulting one or more of the encoders in varying order, a single encoder, a single decoder, etc.); a single transformer; multiple transformers; and/or any other suitable transformers or models.

Additionally or alternatively, the set of models can include other NLP models such as recurrent neural networks (RNNs) (e.g., long short-term memory [LSTM] models, gated recurrent units [GRUs], etc.) and/or any other suitable models.

The model(s) can be any or all of: trained, pretrained, fine-tuned or using other forms of transfer learning (e.g., based on a pretrained model), combined with one or more ontologies (e.g., radiological or other clinical ontology database), and/or any combination of these. In some variations, for instance, the set of models includes one or more trained and/or pretrained models which are fine-tuned based on radiology report language.

The set of models can optionally include and/or interface with a pre-processing module, which functions to clean up and/or otherwise modify data prior to training on and/or processing it. The pre-processing module is preferably implemented prior to or during the training of the model(s), but can additionally or alternatively be implemented on data serving as input to the trained model, and/or be implemented at any suitable time(s) during the method 200 in any suitable way(s).

The set of models can optionally include and/or interface with a post-processing module, which functions to edit and/or otherwise modify one or more outputs produced by the set of models. This can include any or all of: formatting an output (e.g., an impressions section); further improving language styling to better match the style of the radiologist; checking and/or adjusting language for compliance with recommended and/or required language (e.g., medical classification lists such as the International Classification of Diseases and Related Health Problems [ICD], ICD-10, usage of word "indicates" for diagnoses to conform with billing guidelines and/or requirements, merit-based incentive payment system [MIPS] to help with and/or maximize reimbursement, consensus guidelines, etc.); notifying the radiologist of language which potentially may not conform with recommended and/or required language (e.g., as described above, so that the radiologist may manually edit, etc.); and/or any other processing. Additionally or alternatively, any or all of the above can be performed in pre-processing, with the set of models, and/or at any suitable time(s) during the method 100 with any suitable models and/or modules.

The system 200 can optionally further include and/or interface with a radiology platform (e.g., radiology reporting platform, PowerScribe, Fluency for Imaging, etc.), wherein the radiology platform can include a speech recognition system which is equivalently referred to herein as any or all of: a speech recognition platform, a speech transcription system and/or platform, a voice recognition system and/or platform, a voice transcription system and/or platform, a speech-to-text system and/or platform, and/or any other suitable platform including any suitable tools and/or programs. Additionally or alternatively, the radiology platform can include and/or interface with any other software tools and/or programs; interfaces (e.g., set of worklists); and/or any other tools or components.

Additionally or alternatively, the system 200 can include and/or be configured to interface with any or all of: a Picture Archiving and Communication System (PACS) and/or alternative image viewing and image storage platform, a voice recognition platform, an intelligent radiology worklist and/or alternative radiology worklist, a Radiology Information System (RIS) and/or alternative patient tracking platform, an electronic medical record (EMR) database, an electronic health record (EHR) database, a Clinical Information System (CIS) platform and/or alternative management software, a Health Information System (HIS) platform and/or alternative management software, a Laboratory Information System (LIS) platform and/or alternative management software, one or more vendor-neutral archive (VNA) components, and/or any other suitable components.

The system 200 can optionally be tailored to the preferences of a particular radiology group, tailored to the preferences of multiple radiology groups, agnostic of radiology group preferences, tailored to the preferences of an individual radiologist and/or aggregated set of radiologists, tailored to the preferences of a PCP and/or patient, tailored to the preferences of a manager or other healthcare facility entity (e.g., nurse navigator reviewing the radiology worklist(s)), and/or otherwise configured.

In a preferred set of variations, the system 200 is configured to interface with (e.g., integrate with, communicate with, be built on top of, as a virtual machine, etc.) a radiology platform including a speech recognition platform, wherein the method 200 is adapted to integrate with the features of the particular radiology platform.

Additionally or alternatively, the system 200 can be otherwise suitably configured and/or include any other components.

4. Method

As shown in FIG. 1, a method 100 for the computer-assisted implementation of radiology recommendations includes any or all of: receiving a set of inputs S100; determining and/or identifying a set of findings S200; determining a set of follow-up recommendations S300; and triggering an action based on the set of follow-up recommendations S400. Additionally or alternatively, the method 100 can include any other suitable processes performed in any suitable order.

The conventional process for handling follow-up recommendations, such as those associated with incidental findings, has many limitations, which can result in poor outcomes for the patient and the healthcare facility. In conventional workflows, the appropriate follow-up is often defined by consensus guidelines from a number of national clinical societies, though these can vary depending on the radiologist and the clinician's best judgments, as well as on the patient's specific circumstances and associated findings. However, even when the appropriate follow-up is recommended by the radiologist, it often turns out to be very difficult to ensure this follow-up is communicated to the physician responsible for the patient after discharge from the hospital, ensure the follow-up is communicated directly to the patient, and ensure the follow-up is performed according to the recommended timeline, per national consensus guidelines. As a result, many recommendations are not followed up on, which can lead to increased costs, damage to the patient, or even death.

The method 100 preferably functions to enable incidental findings to be consistently and reliably handled, which can involve any or all of: ensuring that they are included in the radiology report; ensuring that a follow-up recommendation is provided based on the incidental finding(s); ensuring that the follow-up recommendations are implemented (e.g., at a current time, at a later time, etc.); and/or ensuring or providing any other outcomes. This can subsequently function to improve patient outcomes through promoting preventative care of the patient (e.g., preventing incidental findings from worsening), prevent missed revenue opportunities for healthcare facilities (e.g., from missed follow-up procedures), reduce healthcare facility liability due to missed follow-up, reduce a mental load of the radiologist and/or physicians in implementing incidental finding follow-up (e.g., by automating any or all of the processes involved in this); and/or perform any other functions. Additionally or alternatively, the method 100 can perform any other functions.

The method 100 is preferably configured specifically for at least incidental findings, and further preferably significant incidental findings, but can additionally or alternatively be performed for non-incidental (e.g., standard, critical, etc.) findings and/or any other information provided in and/or associated with a radiology report.

Examples of incidental findings can include, for instance, but are not limited to, any or all of: pulmonary nodules, persistent opacities, aortic aneurysms, coronary artery calcification, cystic and solid lesions and/or masses in a wide range of organ systems, lytic and blastic lesions (e.g., in the spine), prominent lymph nodes, mural thrombus, dilated biliary ducts, tumors, or any other findings.

The method 100 is preferably performed with a system including one or more computing subsystems configured to process and/or access information, such as radiology images (e.g., scans from a study), radiology reports, patient information (e.g., medical records, medical history, demographic information, associated clinicians such as primary care physician, etc.), healthcare facility information (e.g., on-call physicians, physician contact information, procedure scheduling information, etc.), and/or any other suitable information, such as, but not limited to, a system 200 as described above. The one or computing subsystems can be remote (e.g., cloud-based), local (e.g., at a healthcare facility server), distributed among multiple devices, and/or any combination. Additionally or alternatively, the system can include any other suitable components and/or the method can be performed with any suitable system.

4.1 Method—Receiving a Set of Inputs S100

The method 100 can optionally include receiving a set of inputs S100, which functions to receive information with which to perform any or all other processes of the method 100.

S100 is preferably performed initially during the method 100, but can additionally or alternatively be performed during and/or after another process of the method 100, multiple times during the method 100, in response to a trigger (e.g., request from a user, determination of particular incidental finding and/or follow-up recommendation, etc.), and/or at any other times.

The set of inputs preferably includes a radiology report, which can be completed, partially completed, or any combination. The radiology report can be manually generated (e.g., by a radiologist), automatically generated (e.g., with a trained model), a combination of manually and automatically generated (e.g., report which is manually generated aside from an automatically generated impression section), and/or otherwise suitably generated.

The set of inputs can additionally or alternatively include a set of images associated with a scan and/or study of the patient, where the method includes and/or interfaces with a process which automatically determines a set of findings (e.g., incidental findings) associated with the patient based on the set of images (e.g., with a trained model).

The set of inputs can optionally additionally or alternatively include supplementary information, such as that associated with the patient (e.g., prior studies corresponding to the same incidental finding, prior follow-up recommendations, historical information, etc.), that associated with other patients (e.g., data associated with an aggregated set of patients, etc.), that associated with another user (e.g., radiologist preferences, PCP preferences, radiologist group preferences, etc.), that associated with radiologist consensus guidelines and/or best practices (e.g., for use in creating a lookup table, for use in training a model to automatically determine follow-up recommendations, etc.), and/or any other information.

In a first set of variations, the set of inputs includes a radiology report which is manually generated by a radiologist (e.g., with speech recognition/dictation software, typed, written, etc.). Additionally, the set of inputs can include any other information.

In a second set of variations, the set of inputs includes a radiology report in which one or more sections is automatically generated (e.g., with a set of trained models). Additionally, the set of inputs can include any other information. In a set of specific examples, for instance, the radiology report includes a report in which an impression section is automatically generated with a set of models as described in U.S. application Ser. No. 17/020,593, filed 14 Sep. 2020, which is incorporated in its entirety by this reference.

In a third set of variations, the set of inputs includes a set of images, which are automatically processed in order to determine a set of incidental findings and/or a set of follow-up recommendations (and optionally generate any or all of the radiology report).

Additionally or alternatively, S100 can include any other suitable processes.

4.2 Method—Determining and/or Identifying a Set of Findings S200

The method 100 can optionally include determining and/or identifying a set of findings S200, which functions to identify findings with which to prompt and/or perform the subsequent processes of the method 100. Additionally or alternatively, S200 can function to perform any or all of: identifying incidental findings in particular and/or distinguishing incidental findings from non-incidental findings and/or other information; identifying significant incidental findings (e.g., incidental findings associated with a follow-up recommendation and/or advised to include a follow-up recommendation) and/or distinguishing incidental findings from insignificant incidental findings; characterizing (e.g., classifying) an incidental finding as a particular type of incidental finding; detecting that one or more incidental findings is missing from the radiology report; and/or any other functions.

S200 is preferably performed in response to and/or based on S100, but can additionally or alternatively be performed in absence of S100 (e.g., initially in the method 200), in response to one or more processes of the method 200, in parallel with and/or at least partially overlapping with another process of the method 200, in response to a trigger, multiple times during the method 200 (e.g., at a predetermined frequency, continuously, etc.), and/or at any other times and/or combination of times.

S200 is preferably performed at least partially automatically and further preferably without any manual user (e.g., radiologist, patient, etc.) input and/or actions, but can optionally additionally or alternatively be performed partially of fully with manual input.

The set of findings identified in S200 preferably includes incidental findings, further preferably clinically significant incidental findings (e.g., associated follow-up and/or a follow-up recommendation), but can additionally or alternatively include clinically insignificant findings, non-incidental findings (e.g., normal findings, abnormal findings, etc.), and/or any other information.

Identifying the set of findings (e.g., only incidental findings, all findings, etc.) can include any or all of: identifying the findings based on the images in a radiology study; identifying the radiologist's inclusion of an incidental finding or other finding in a radiology report (e.g., in the "findings section"); characterizing, classifying, and/or distinguishing different types of findings; and/or can include any other suitable processes for identifying an incidental finding or any other finding. Additionally or alternatively, S200 can include identifying any other information in a radiology report and/or any other information associated with incidental findings. For instance, S200 can include identifying follow-up recommendations associated with an incidental finding for a report in which the radiologist did include a follow-up recommendation for the incidental finding.

S200 is preferably performed at least partially automatically, such as with one or more trained models (e.g., machine learning models, deep learning models, neural networks, etc.). In preferred variations, for instance, a set of trained models can be used to perform any or all of: determining incidental findings based on radiology images, characterizing incidental findings (e.g., as critical vs. non-critical, as significant vs. not significant, versus non-incidental findings, etc.), checking for the presence of and/or identifying incidental findings in a radiologist report, and/or performing any other processes. The trained models are preferably machine learning models (e.g., deep learning models, neural networks, regression models, reinforcement learning models, inverse reinforcement learning models, etc.). Additionally or alternatively, untrained models and/or algorithms (e.g., rule-based, programmed, etc.), lookup tables and/or databases, human input, and/or any other suitable tools can be used for any or all of these processes.

In a preferred set of variations, S200 includes processing a radiology report (e.g., a typed radiology report, the audio of a dictated radiology report, a written radiology report, etc.) received in S100 with a set of one or more trained models to detect the presence of language (e.g., words, keywords, phrases, etc.) which corresponds to (e.g., is predicted to correspond to) a set of findings. The trained model(s) preferably includes a neural network, and further preferably a neural network configured for NLP (e.g., a trained transformer model), such as a neural network configured to detect language (e.g., words, phrases, etc.) associated with pathologies typically corresponding to a desired category of findings (e.g., incidental findings) and/or any other language corresponding to the desired categories of findings. In a first specific example, S200 further includes identifying a particular section (e.g., findings section) in which the findings are most likely to be described, and then processing that particular section to detect if and/or which findings might be present. In a second specific example, S200 is performed in absence of detecting a particular section (e.g., processes multiple sections of the report, processes all sections of the report, etc.).

S200 further preferably includes processing any or all of the outputs of the trained models and/or algorithms with rule-based logic (and/or any other programmed processes). In some variations, for instance, upon detecting that a portion of the radiology report (e.g., text, string of text, sentence, sentences, phrase, set of words, etc.) is associated with (and/or predicted to be associated with) a finding and/or a particular type of finding (e.g., incidental finding), rule-based logic can be implemented to determine a set of features associated with that text, where the set of features preferably functions to determine if a follow-up recommendation is needed (and/or what type of follow-up recommendation is needed). The features can include, for instance, any or all of the following features associated with a finding (e.g., a pathology associated with the finding): size parameters (e.g., volume, length, width, depth/thickness, diameter, etc.); shape parameters (e.g., regular, irregular, circular, elongated, ovoid, etc.); quantity parameters (e.g., a number of detected polyps); location parameters (e.g., relative to anatomical landmarks, relative to an area of concern, etc.); and/or any other parameters. These can be detected/determined based on any or all of: keywords associated with these features (e.g., "size," "diameter," "millimeters," "milliliters," "circular," "irregular," "symmetric," "one," "two," "single," "multiple," "proximal," "distal," etc.); the detection of numbers (e.g., as opposed to words); the proximity of feature words to other words of the sentence; and/or the features can be detected in any other way(s) (e.g., with the trained models). Alternatively, S200 can be performed in absence of detecting any or all of these features.

Rule-based logic can additionally or alternatively be used to determine contextual features associated with the findings and/or features of the findings, which can function to determine if any or all of the features (and/or findings) are negated (e.g., in order to not prompt one or more follow-up recommendations, in order to select appropriate follow-up recommendations, in order to finalize the set of incidental findings which are present, etc.). In s set of examples, for instance, determining the contextual features includes checking for a set of negation words (e.g., predetermined negation words such as "not," "no," etc.) proximal to the features and/or findings (e.g., within the same sentence, immediately prior to, etc.), but can additionally or alternatively include any other processes. Additionally or alternatively, contextual features can be determined with another process (e.g., with a trained model), S200 can be performed in absence of determining contextual features, and/or S200 can include any other processes.

S200 can optionally additionally or alternatively include characterizing any or all of the detected findings (e.g., incidental findings), such as by assigning any or all of the detected findings to one or more categories, such as categories which correspond to (e.g., map to) a particular type of finding; a particular class and/or type of recommendation (e.g., based on radiology consensus guidelines, best practices, predetermined associations, etc.); and/or any other categories. Characterizing the findings can be performed with any or all of: a decision tree or other rule-based process, lookup table, equation and/or formula and/or algorithm, model, and/or any other tools.

Additionally or alternatively, S200 can process the set of inputs with only programmed/rule-based processes, only with trained processes, and/or with any other processes or combination of processes.

In identifying an incidental finding, S200 can optionally include characterizing the incidental finding into a set of classes and/or groupings of incidental findings. The set of classes preferably functions to inform subsequent processes of the method, such as which follow-up is most suitable, which actions should be triggered based on the incidental finding, but can additionally or alternatively be used in any other suitable ways. The set of classes can be determined based on any or all of: the finding itself (e.g., type of incidental finding, body region, associated condition, etc.), other findings (e.g., comorbidities, etc.), the radiology report (e.g., whether the radiologist noted the incidental finding, whether the radiologist did not note the incidental finding, whether the recommendations section includes follow-up associated with the incidental finding, whether the recommendations section does not include follow-up associated with the incidental finding, etc.), patient information (e.g., historical information, prior radiology reports, demographic information, pre-existing conditions, etc.), healthcare facility information (e.g., availability/ability to perform follow-up), physician information (e.g., which physicians the patient is under the care of), an identifier of the incidental finding (e.g., human radiologist, model and/or algorithm, etc.), consensus guidelines (e.g., dictating appropriate and/or recommended follow-up for an incidental finding), and/or any other suitable information. Additionally or alternatively, any or all of the classes described below can correspond to scenarios which the method 100 is configured to detect and/or be configured to perform within.

The set of classes can optionally include a first class (Class I) indicating that one or more incidental findings were identified by a radiologist in the radiology report and that accurate consensus guideline recommendations were provided by the in the radiology report. In specific examples, for instance, this class can indicate that the recommendations can be relayed in S400 to the patient's outpatient physician(s), to the patient, and also tracked for future follow-up, and can optionally indicate that S300 can be skipped. Additionally or alternatively, the class can be used in any other suitable ways.

The set of classes can optionally additionally or alternatively include a second class (Class II) indicating that one or more incidental findings were identified by a radiologist in the radiology report, but that recommendations associated with the incidental findings were not clearly provided. In specific examples, this can function to trigger the performance of S300 (e.g., after the radiologist has finished the report, while the radiologist is still working on the report, independent of the report's completion, etc.), wherein the recommendations can be determined any or all of: automatically (e.g., with one or more trained models), by a radiologist (e.g., the radiologist completing the report, a different radiologist, etc.), or any combination. In a first specific example of Class II characterization, the method can include determining that missing recommendations need to be identified, and in response, re-introducing the study back into the radiologist's queue for review, such as with a label or tag point the radiologist to the incidental finding. Once the radiologist adds the recommendation (e.g., in a report addendum including the recommendation), it can be used to trigger one or more actions in S400, such as being provided to the patient's outpatient physician(s), to the patient, and/or tracked for future follow-up. In a second specific example, missing recommendations can be identified automatically and indicated to the radiologist before the radiologist finalizes his or her report dictation, so that the radiologist can include the recommendation prior to signing the report. Additionally or alternatively, Class II incidental findings can be otherwise characterized and/or used.

The set of classes can optionally additionally or alternatively include a third class (Class III) indicating that incidental findings were missed by the radiologist in the report. This can be identified, for instance, automatically with a set of trained models (e.g., machine learning models) review the radiology images and flag significant incidental findings that need follow-up (e.g., based on consensus guideline criteria). In specific examples, the study can optionally be added back to the radiologist queue for review, as indicated for instance with a tag and/or label. In an event that the radiologist confirms that this is a significant incidental finding, he or she can add the incidental finding and an associated recommendation to the report (e.g., in a report addendum to the recommendations section). In a second specific example, one or more trained models can review the images and flag significant incidental findings immediately after study image acquisition, so that any missed incidental findings can be brought to the radiologist's attention before the radiologist finalizes his or her report dictation. Additionally or alternatively, the recommendations can be automatically determined (e.g., in S300), and/or Class III incidental findings can be otherwise characterized and/or used.

Figure 3:
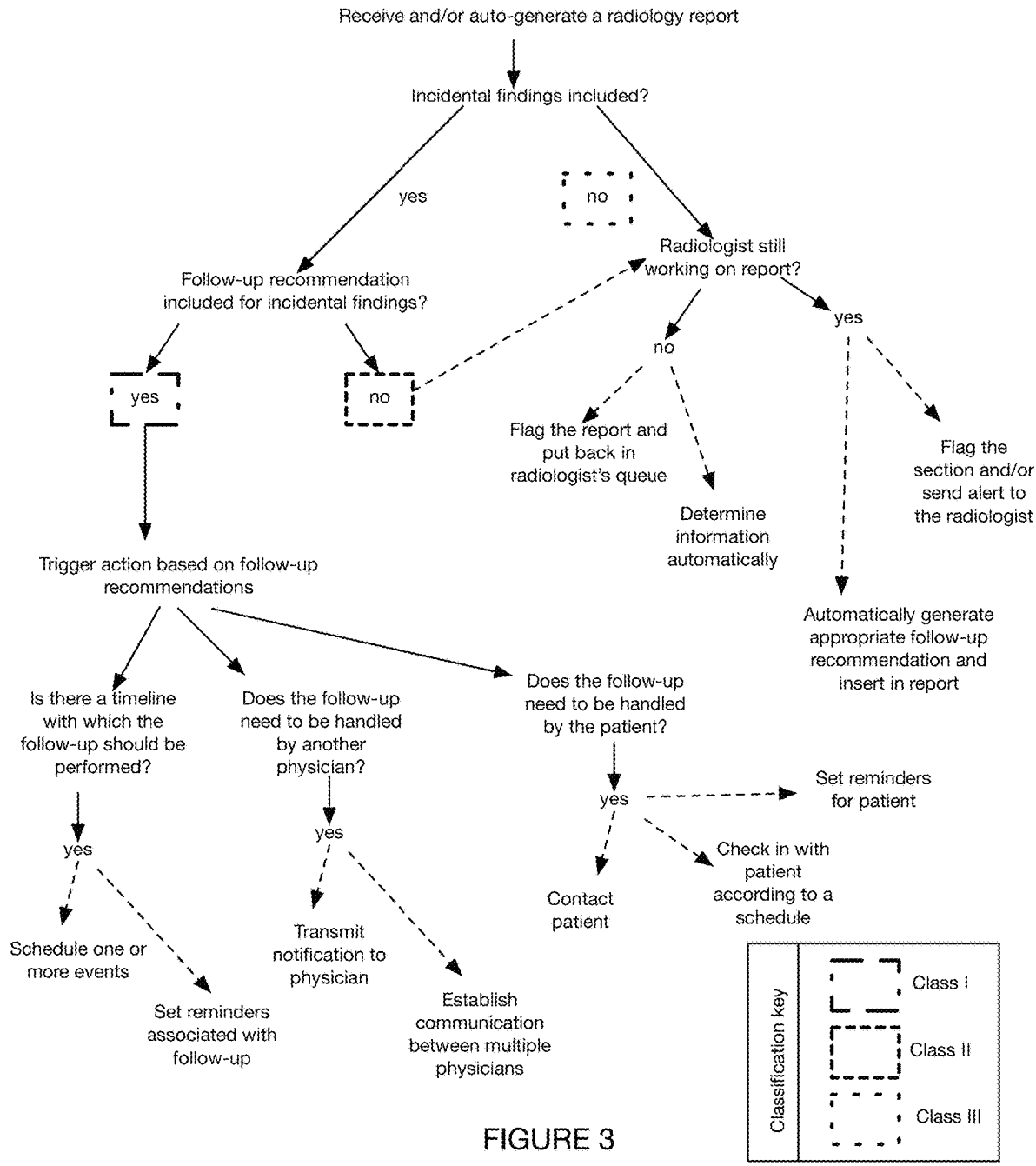
FIG. 3 depicts a variation of a decision tree in performing any or all of the method 100.

In the specific example shown in FIG. 3, a decision tree can be used in assigning one of a set of classes to the radiology report.

Additionally or alternatively, the incidental findings can be characterized into any other suitable classes and/or combination of classes.

Further additionally or alternatively, characterizing the incidental findings can include comparing an incidental finding with a set of criteria and/or thresholds (e.g., criteria indicating whether or not a follow-up recommendation should be made) and/or any other suitable processes.

S200 can additionally or alternatively include any other suitable processes.

4.2 Method—Determining a Set of Follow-Up Recommendations S300

The method 100 can include determining a set of follow-up recommendations S300, which functions to identify and/or formulate a set of follow-up recommendations associated with any or all of a set of findings (e.g., incidental findings) (e.g., as determined in S200). Additionally or alternatively, S300 can function to automatically locate the set of follow-up recommendations within a radiology report; identify that one or more follow-up recommendations is missing and/or incomplete; create and/or complete one or more follow-up recommendations; identify a mismatch between the set of findings and the set of follow-up recommendations; and/or perform any other functions.

Any or all of S300 can optionally be performed in response to S200, such as based on the set of findings determined in S200. Any or all of S300 can optionally additionally or alternatively be performed in absence of S200, such as without identifying and/or without first identifying any or all of a set of findings. Further additionally or alternatively, any or all of S300 can performed prior to S200, as part of S200 (e.g., in classifying the set of incidental findings), as part of S400, multiple times (e.g., continuously, at a predetermined frequency, at a random set of intervals, in response to a trigger, etc.), and/or at any other suitable times. Additionally or alternatively, the method 100 can be performed in absence of S300.

S300 is preferably at least partially performed automatically, such as with a set of trained models and/or algorithms. Additionally or alternatively, any or all of S300 can be performed with rule-based logic and/or algorithms, or can otherwise be suitably performed.

In variations in which S200 includes classifying one or more incidental findings, S300 is further preferably performed in response to the classification. Additionally or alternatively, S300 can be performed in absence of a classification, and/or at any other time(s).

The follow-up recommendations preferably include those which corresponding to an incidental finding, but can additionally or alternatively include follow-up recommendations corresponding to another finding (e.g., associated with the primary reason for the study), all findings (e.g., to be distinguished later), and/or any combination of findings.

In a preferred set of variations, S300 is configured to detect and track follow-up recommendations for only incidental findings and/or a subset of incidental findings (e.g., significant incidental findings), as findings associated with the primary reason for the study will be already handled and/or appropriately followed up on according to existing procedures and/or protocols.

In a second set of variations, all follow-up recommendations are determined and/or tracked in S300.

Determining the set of follow-up recommendations can include, for instance, any or all of: checking for and/or locating existing follow-up recommendations within a radiology report; verifying that one or more follow-up recommendations are associated with an incidental finding (e.g., critical incidental finding); verifying that each incidental finding is either associated with a follow-up recommendation or that no follow-up recommendation is required; selecting and/or formulating one or more follow-up recommendations; flagging a radiology report for review and insertion of follow-up recommendations by a radiologist (e.g., based on a Class II classification, based on a Class III classification, etc.); and/or any other suitable processes.

S300 is preferably at least partially performed with a set of trained models (e.g., machine learning models, deep learning models, neural networks, NLP models, trained transformer models, etc.), which can individually and/or collectively function to detect recommendations within the radiology report. This can additionally function to detect recommendations from anywhere within a report, such as in cases in which recommendations are not necessarily delegated to particular sections or locations within a report. Additionally or alternatively, the set of trained models can be used for any other processes (e.g., as described below), such as, but not limited to: generating recommendations, completing recommendations, classifying recommendation, selecting and/or triggering an output/action based on the recommendation(s), and/or any other processes.

Additionally or alternatively, any or all of S300 can be performed with a set of rule-based and/or programmed processes (e.g., rule-based logic, decision trees, etc.), manual processes, any other processes, and/or any combination of processes.

The set of trained models is preferably configured to process language (e.g., typed text, written text, dictated speech, etc.) in the radiology report (e.g., as described above), but can additionally or alternatively be configured for image-based processing and/or any other types of processing. The set of trained models further preferably includes one or more neural networks (e.g., NLP neural networks, trained transformer model, etc.) configured to detect different types of entities in the radiology report, such as: keywords, contextual language (e.g., in surrounding text), a combination of keywords and contextual language, features, and/or any other information. Additionally or alternatively, any or all of the language processing can be performed with rule-based and/or programmed processes, a combination of processes, and/or any other processes.

S300 can optionally include checking for and/or locating a set of follow-up recommendations S310, which functions to determine which follow-up recommendations are associated with the radiology report, and can additionally function to trigger the appropriate outputs and/or actions in S400, detect if any follow-up recommendations are missing, and/or can perform any other functions. S310 (and/or any other processes of S300) is preferably at least partially performed with a set of trained models (e.g., as described below, as described above, etc.), but can additionally or alternatively be performed with one or more programmed and/or rule-based processes (e.g., as described below, as described above, etc.), and/or with any other processes.

S300 can optionally additionally or alternatively include characterizing any or all of a set of follow-up recommendations S320, which functions to inform any or all of the remaining processes of the method 100.

In a set of variations, any or all of the radiology report is processed with a transformer-based model that works at the sentence level, which characterizes (e.g., classifies) individual sentences. The characterization preferably indicates whether or not the sentence (or other text structure/amount) corresponds to a follow-up recommendation, but can additionally or alternatively determine (e.g., specify) a type of recommendation (e.g., follow-up imaging, examination, specialist referral, bloodwork, etc.) associated with the sentence; a particular finding and/or type of finding (e.g., incidental finding classification, significant incidental finding classification, particular finding classification, etc.); a feature associated with the follow-up recommendation and/or finding; a level of completion associated with the recommendation; and/or any other characterization(s).

The set of models (e.g., transformer-based model, other model(s), etc.) can further optionally process neighboring text (e.g., prior sentence(s), subsequent sentence(s), text within the sentence, other paragraphs, other sections, etc.) to determine an overall context associated with the sentence, which can be used to refine the individual sentence characterizations (e.g., to match the overall context). In specific examples, for instance, if it is unclear from an individual sentence what a characterization (e.g., classification) might be (e.g., based on an uncertainty calculation exceeding a predetermined threshold, based on a confidence metric falling below a predetermined threshold, etc.), an overall context (e.g., overall paragraph, neighboring sentences, whole report, etc.) can be determined to confirm, reject, alter, and/or otherwise examine the characterization. The context is preferably determined based on processing one or more sentences (or other strings of text) proximal to (e.g., immediately prior, immediately after, within a predetermined number of sentences within, etc.) a sentence and/or other string of text associated with a candidate recommendation, but can additionally or alternatively be located elsewhere in the radiology report and/or otherwise defined. Additionally or alternatively, a context can be determined with one or more rule-based processes, S300 can be performed in absence of determining a context, and/or S300 can be otherwise suitably performed.

The set of models (e.g., transformer-based model as described above, separate transformer-based model, transformer-based model with a text classifier, etc.) can further optionally function to determine one or more anatomical features (e.g., references to a particular anatomical feature) associated with the sentence(s) (or other text), which can function to determine, for instance, which body region(s) a recommendation and/or finding is associated with. In specific examples, for instance, determining an anatomical classification and/or set of features associated with the sentence can function to determine which anatomical region a recommendation and/or associated finding corresponds to (e.g., whether or not a detected nodule is associated with the liver versus the lung). Additionally or alternatively, S300 can be performed in absence of detecting anatomical features; anatomical features can be detected during S200 and/or with another process (e.g., processing other sections of the radiology report, processing patient and/or study metadata, etc.) of the method; and/or anatomical features can be determined in any other way(s).

S300 further preferably includes a set of rule-based and/or programmed processes (e.g., implementing rule-based and/or hard-coded logic, etc.), which can function to determine a set of features associated with the detected recommendations. The set of features preferably includes a particular finding (e.g., which pathology, incidental finding, etc.) that the recommendation corresponds to. This can be used, for instance, to determine if any or all of the findings determined in S200 are missing a recommendation, to determine an optimal and/or accurate set of actions/outputs to be triggered in S400, and/or can perform any other functions.

Additionally or alternatively, the set of features can include any or all of: a set of temporal features associated with the recommendation (e.g., time frame in which the follow-up recommendation should be performed); a type of recommendation (e.g., a recommended scan such as a CT scan, bloodwork, a specialist appointment, an examination, etc.); and/or any other recommendation features. These can be used, for instance, to produce a structured output which can be used downstream in determining and/or scheduling any or all of the actions and/or outputs in S400.

In a set of examples, for instance, S300 includes detecting (e.g., with hard-coded, rule-based logic; with trained models; with decision trees; etc.) one or more temporal features associated with the follow-up recommendation, such as a timeline prescribed for a follow-up action. This is preferably determined based on the detection of one or more temporal keywords (e.g., "months," "days," "weeks," "before," "after," a month name, a date, a year, etc.) and/or phrases, but can additionally or alternatively be determined based on other information, with a trained model, and/or with any other tools.

In another set of examples, S300 includes detecting a type of follow-up (e.g., type of action and/or next step) associated with a recommendation and/or distinguishing between types of follow-up, such as detecting a recommendation for any or all of: further imaging, an examination (e.g., with a PCP, with a specialist, etc.), laboratory work, a procedure, and/or any other follow-up. The type of follow-up can be determined with any or all of: the detection of one or more keywords (e.g., "imaging," "MRI," "CT," "lab work," "lab," "bloodwork," "appointment," "exam," "procedure," surgery," etc.) and/or phrases; a trained model; and/or with any other tools.

Additionally or alternatively, S300 can optionally include detecting a level of completion associated with any or all of the set of follow-up recommendations S330, which functions to ensure that accurate and comprehensive follow-up actions/outputs are triggered in S400. This can optionally additionally include detecting that one or more follow-up recommendations is missing from a radiology report. In some variations, for instance, S330 includes determining whether or not a recommendation is complete and optionally further determining which components are missing from an incomplete recommendation. This is preferably performed with a rule-based and/programmed process, such as rule-based logic which identifies if and/or what components are missing from the recommendation itself (e.g., based on referencing consensus guidelines, a lookup table, a predetermined set of recommendation components, a decision tree, etc.) and if they are missing, S300 can optionally include processing contextual information (e.g., other sections of the radiology report) to find and/or infer the missing information. Additionally or alternatively, S300 can include referencing other information (e.g., consensus guidelines, a corpus of previously generated radiology reports, etc.) to detect that a recommendation is incomplete (and/or to complete the recommendation), and/or any other processes. In another set of variations, S330 includes associating any or all of the set of follow-up recommendations with a corresponding finding, which can function to check for and/or confirm that each incidental finding in the report (e.g., as determined in S200) has an associated follow-up recommendation (if applicable).

Figure 5:
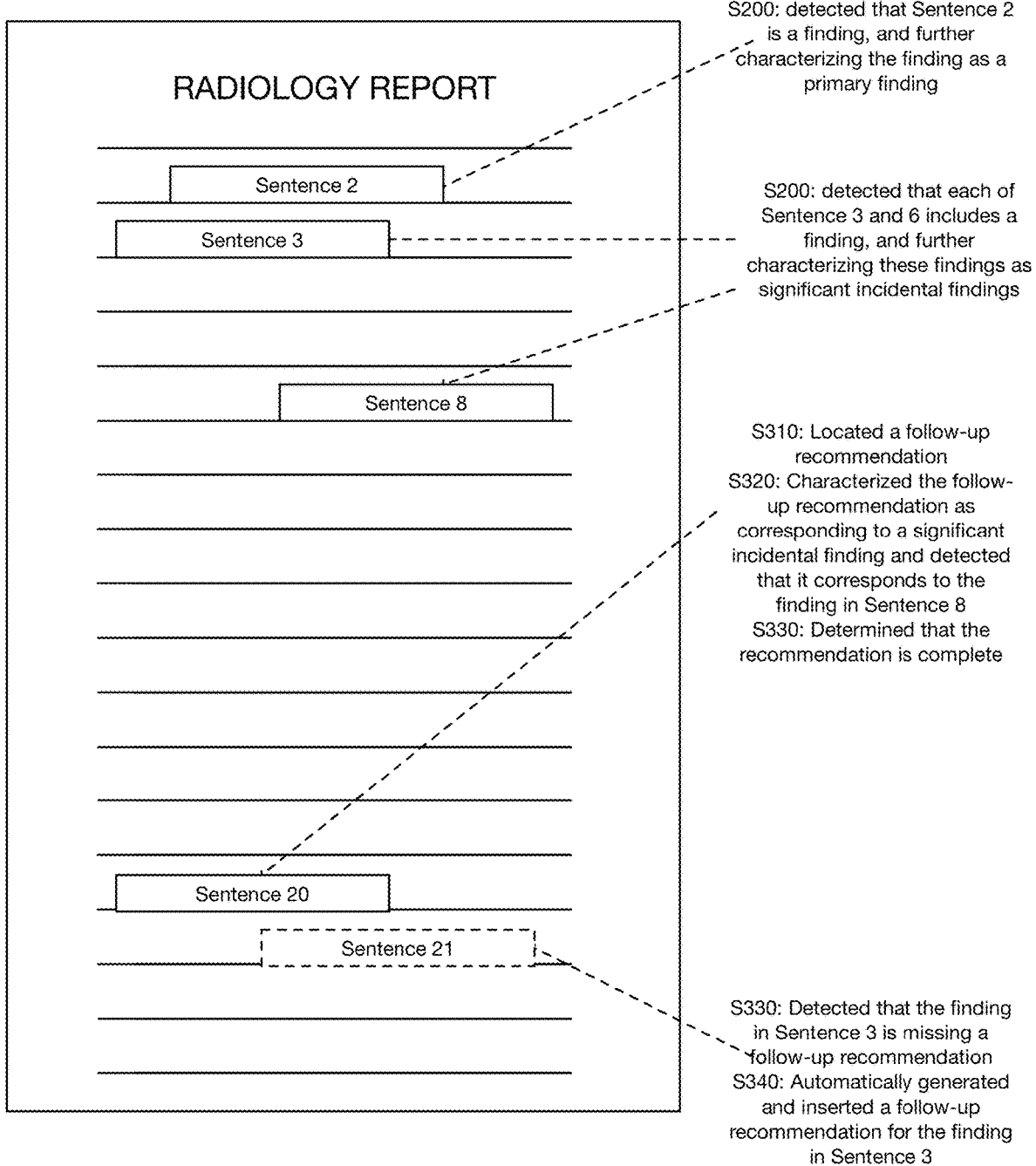
FIG. 5 depicts a variation of the processing a radiology report.

In specific examples (e.g., as shown in FIG. 5), this includes comparing the results of S200 with follow-up recommendations detecting in S300 (e.g., in S310, in S32o, etc.) to determine if any follow-up recommendations are missing, if any follow-up recommendations do not have an associated incidental finding (e.g., for flagging the report, for further searching, for consolidation of follow-up recommendation, for removing redundancies in follow-up recommendations, etc.), if each of the follow-up recommendations is appropriate for the given finding, and/or if any other scenarios exist.

S300 can optionally additionally include completing (e.g., automatically completing) any or all of the set of recommendations (e.g., incomplete recommendations) and/or generating (e.g., automatically generating) part or all of any or all of the set of recommendations S340, which can function to increase an accuracy and/or comprehensiveness of the outputs and/or actions triggered in S400; reduce a time and/or human effort required to complete a radiology report; and/or can perform any other functions. This is preferably performed automatically (e.g., by referencing a lookup table, by implementing a trained model, etc.), but can additionally or alternatively be performed manually (e.g., by flagging a radiologist to complete and/or add the recommendation), and/or any combination. Completing and/or generating a recommendation can be performed with any or all of: rule-based and/or programmed processes (e.g., referencing a lookup table, implementing hard-coded logic, processing a decision tree, etc.); trained models (e.g., generating text with a machine learning model, etc.); one or more templates; any combination; and/or any other processes. The completed and/or generated (e.g., fully generated) recommendation is preferably determined in accordance with (e.g., based on) any or all of: radiology consensus guidelines (e.g., Fleischner guidelines), radiology group guidelines and/or conventions, best practices, user and/or group and/or facility preferences, and/or any other information. In some variations, for instance, the type and/or content of any or all follow-up recommendations are determined in accordance with the preferences and guidelines of the associated radiology group.

In variations in which a set of follow-up recommendations are generated, the follow-up recommendations can be any or all of: inserted into a predetermined section (e.g., impression section) of the radiology report; inserted into a most relevant section; not inserted into the radiology report (e.g., submitted as an addendum, inserted into a separate document, etc.); and/or otherwise utilized.

Any or all of S300 can optionally include assessing a type of imaging (e.g., CT, MRI, ultrasound, etc.) associated with the scan/study and/or any other features of the study, which can function to specify what the follow-up recommendations can and/or should include (e.g., based on consensus guidelines, based on which regions of the body are able to be seen and therefore which findings would be possible to detect, etc.). This can further function to inform which follow-up recommendations to check for, to inform how to complete and/or generate follow-up recommendations, to determine which components In a first set of variations (e.g., as shown in FIGS. 2A-2D), S300 includes reviewing a radiology report and checking for one or more follow-up recommendations corresponding to incidental findings. In an event that the follow-up recommendations are present, the report can be flagged (e.g., with an HL7 flag) for triggering one or more actions in S400. In an event that the follow-up recommendations are not present, but should be based on the presence of critical incidental findings, the report can be any or all of: sent back to the radiologist for review and the addition of follow-up recommendations, annotated to include a set of follow-up recommendations determined with artificial intelligence (e.g., a set of trained models) and optionally sent back to the radiologist for review, and/or otherwise modified.

In a second set of variations, a first sub-process (e.g., with trained models) of S300 first detects individual sentences that correspond to a recommendation (e.g., contain recommendation-like text through freeform language processing, templated language with references to consensus guidelines and/or publications, etc.), which is followed up with a second sub-process (e.g., rule-based logic) to determine one or more features associated with the set of recommendations. In specific examples, the sentences are detected based on a trained model (e.g., trained transformer model) and further processed with rule-based logic to determine what features (e.g., temporal features, type of recommendation, etc.) are associated with the recommendation. In an event that any or all of the components are missing, the recommendation can optionally be automatically completed (e.g., with a trained model, with template language and a lookup table, etc.).

In a third set of variations, any or all of a set of follow-up recommendations are automatically generated upon detecting that an incidental finding in the radiology report is not associated with a follow-up recommendation.

4.3 Method—Triggering an Action Based on the Set of Follow-Up Recommendations S400

The method 100 preferably includes triggering an action based on the set of follow-up recommendations S400, which functions to ensure that the follow-up recommendations are reliably and consistently integrated within a care plan for the patient, so that they are not overlooked, missed, or forgotten. This can subsequently function to maintain and/or improve a health of the patient (e.g., by not ignoring incidental findings, by treating incidental findings, etc.); minimizing and/or reducing the mental burden of tracking incidental findings for clinicians, radiologists, and/or healthcare facilities; increasing a number of follow-up procedures performed; and/or can perform any other suitable functions.

S400 can further function to be customized for user preferences and/or integrated according to user (e.g., radiology group, healthcare system, radiologist, patient, PCP, etc.) requests, needs, and/or existing infrastructure. This can include, for instance, any or all of: enabling customization of the recommendation types which are tracked; enabling customization of the types of incidental findings which are detected and/or assigned to have follow-up; integrating into existing Radiology Information System (RIS) platforms, Electronic Health Record (EHR) platforms, Picture Archiving and Communication System (PACS) platforms, and/or other software/databases associated with the user and/or customer; integrating with existing provider and/or patient portals; integrating with existing scheduling systems; and/or any can enable any other customizations and/or integrations.

The actions are preferably determined and/or selected based the incidental findings and/or the follow-up recommendations, but can additionally or alternatively be determined based on any or all of: guidelines, the patient's specific circumstances and/or condition (e.g., comorbidities), the patient's insurance and/or financial situation, other findings, patient historical information (e.g., prior imaging to show progression of finding), and/or any other information.

Examples of actions and/or outputs being triggered can include, but are not limited to, any or all of: adding follow-up recommendations to a set of worklists or other interfaces; transmitting a message or other output (e.g., text, physical mail, email, message in a healthcare platform, reminder message for user to schedule follow-up examination, etc.) to a user (e.g., patient, PCP or other physician of the patient, radiologist, other user, potential PCP, etc.); flagging and/or further processing the case (e.g., study) to initiate facilitating the assignment of a PCP to a patient without a PCP (e.g., generating a referral, contacting the patient and/or PCP, establishing communication between the patient and a PCP, etc.); generating a imaging order (e.g., over RIS, with a fax, with a message, with a scheduling tool, etc.) for initiation and/or confirmation (e.g., by the patient, by the PCP, etc.); providing customizable interfaces (e.g., worklists) and/or analytics to a manager (e.g., nurse navigator, facilitator, radiology assistant, radiology department manager, head of a radiology group, etc.) or other user; and/or any other actions/outputs can be triggered.

S400 is preferably performed in response to S30o, but can additionally or alternatively be performed in response to another process of the method (e.g., S200), prior to any processes of the method, multiple times (e.g., at a predetermined frequency, at a random set of intervals, etc.), and/or at any other suitable time(s).

S400 is preferably performed at least partially automatically, wherein any or all of the triggers are automatically set and implemented (e.g., according to a schedule, based on a detected trigger, etc.). Additionally or alternatively, S400 can be performed manually, and/or any combination of manually and automatically.

S400 can optionally include communicating the set of incidental findings and/or the associated follow-up recommendations, which can function to ensure that an appropriate entity is notified of this information. Communicating the set of findings can optionally include generating (e.g., auto-generating) and/or transmitting (e.g., auto-transmitting) one or more notifications (e.g., messages, alerts, etc.), wherein the notifications can be transmitted to any or all of: a physician/clinician (e.g., emergency room physician, patient's primary care physician, specialist physician, etc.), a healthcare facility and/or associated database (e.g., to be included in patient's medical record); the patient (e.g., to make them aware of follow-up they should initiate); a computing system (e.g., for further processing, for tracking, etc.); and/or any other individuals and/or entities.

In some variations, for instance, S400 includes automatically notifying (e.g., through a text message, email, call, mail, etc.) the patient of his or her incidental findings and the associated follow-up recommendations. Additionally or alternatively, S400 can include automatically notifying the patient's primary care physician and/or any other outpatient providers of the incidental findings and/or follow-up, such that the physician can be made aware and take any measures that he or she sees fit for the patient.

S400 can optionally additionally or alternatively include establishing communication between multiple entities. This can include communication between the patient and a physician (e.g., primary care physician) such that the physician can provide guidance on follow-up steps; between multiple physicians (e.g., between an attending physician and an outpatient physician, between an ER physician and an outpatient provider, etc.); between a radiologist and a physician (e.g., between the radiologist filling out the report and the patient's primary care physician, between the radiologist filling out the report and an attending physician at the same healthcare facility for immediate treatment, etc.); between systems and/or databases (e.g., through an HL7 message); and/or between any other entities. Establishing communication can include any or all of: providing contact information; setting up a message thread; sending notifications; initiating a phone call and/or conference call; sending a fax (e.g., faxed discharge summary, faxed discharge order, etc.); and/or any other communication can be suitably established.

In a first variation, S400 includes communicating the incidental findings and the follow-up recommendations to a physician responsible for the patient after discharge from the healthcare facility performing the imaging. This can include a message, call, alert, update to the patient's medical file, and/or any other suitable communication.

In a second variation, S400 includes communicating the follow-up recommendations directly to the patient.

Figure 7A:
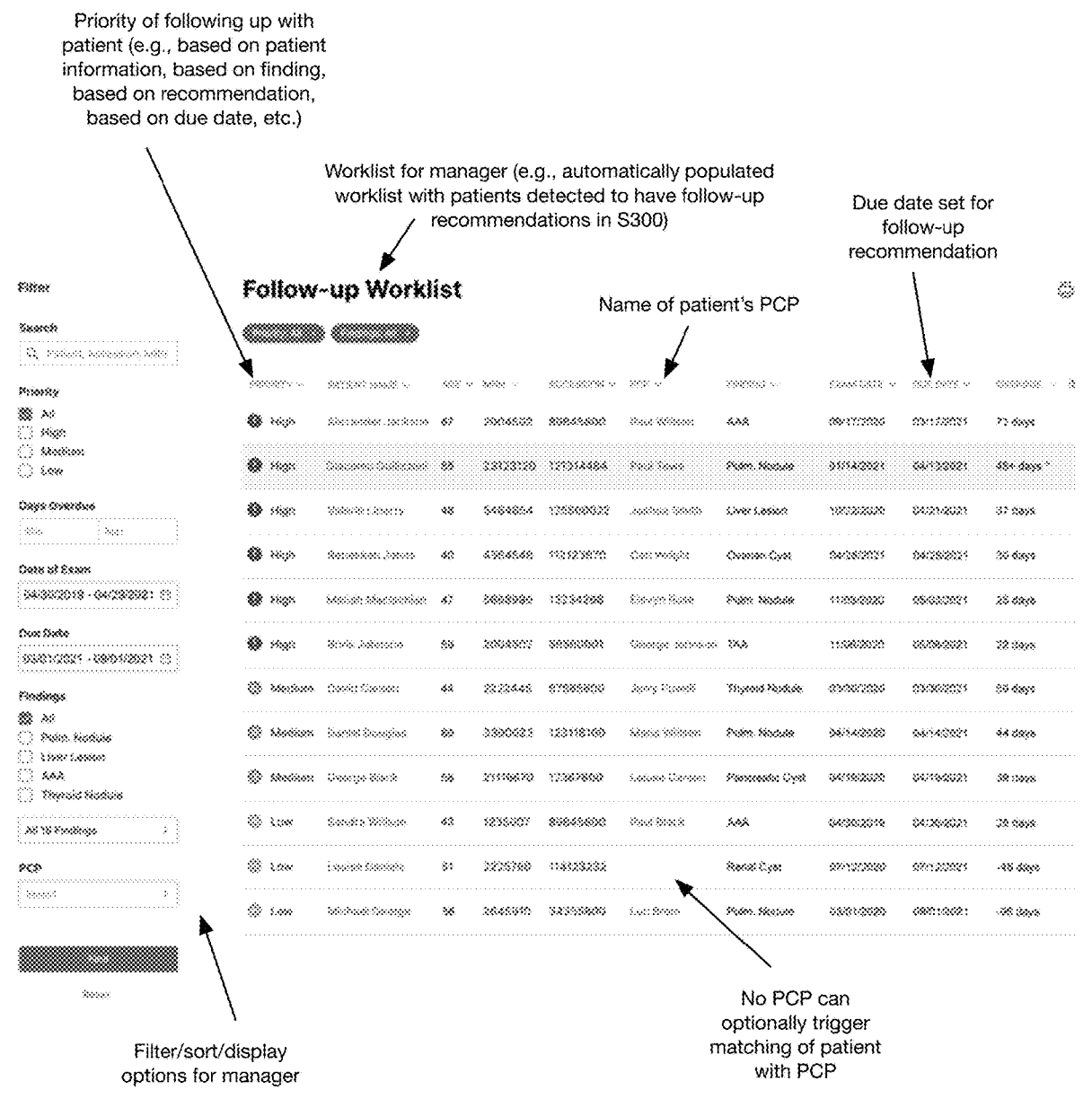
Figure 7B:
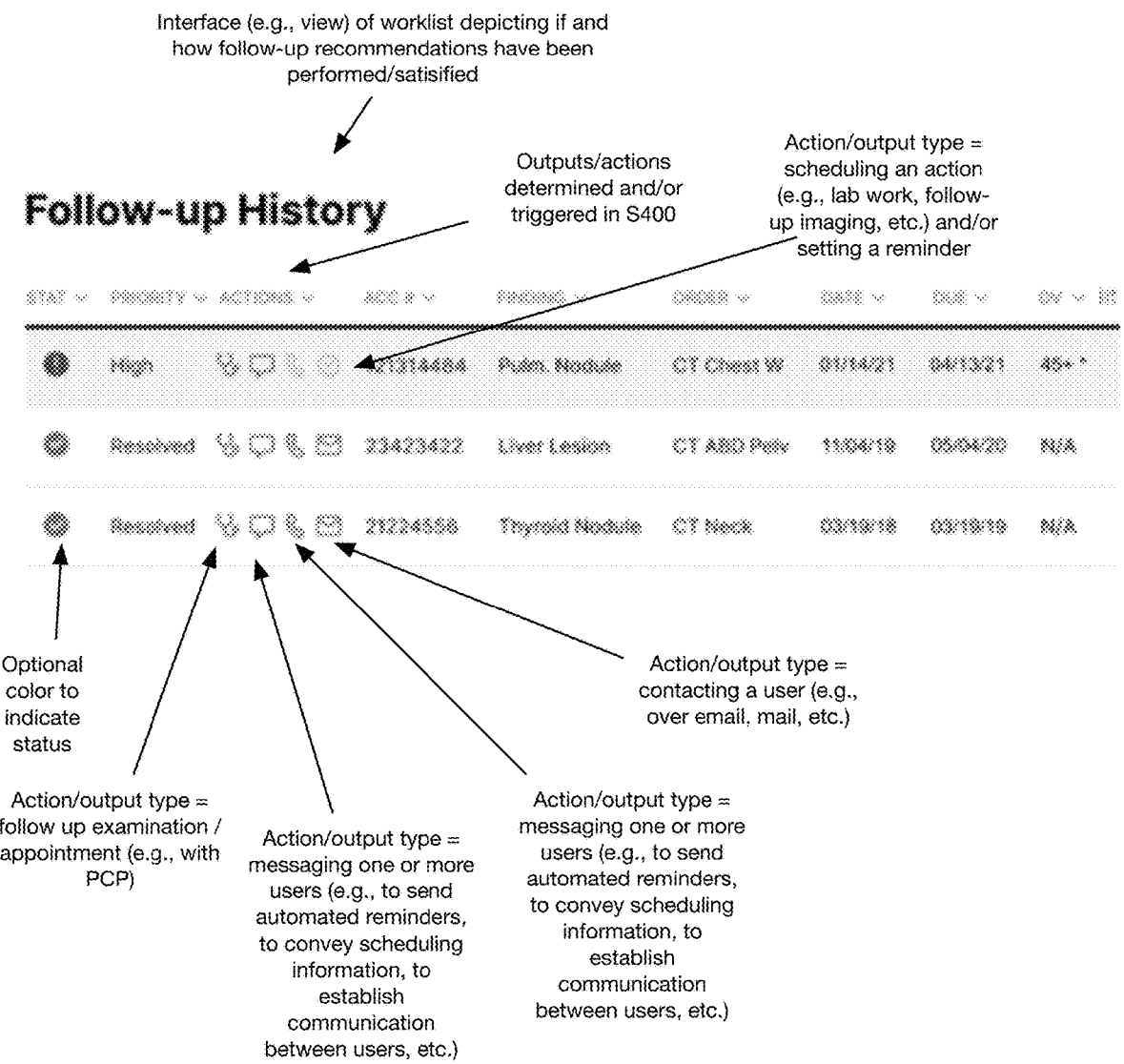
Figure 7C:
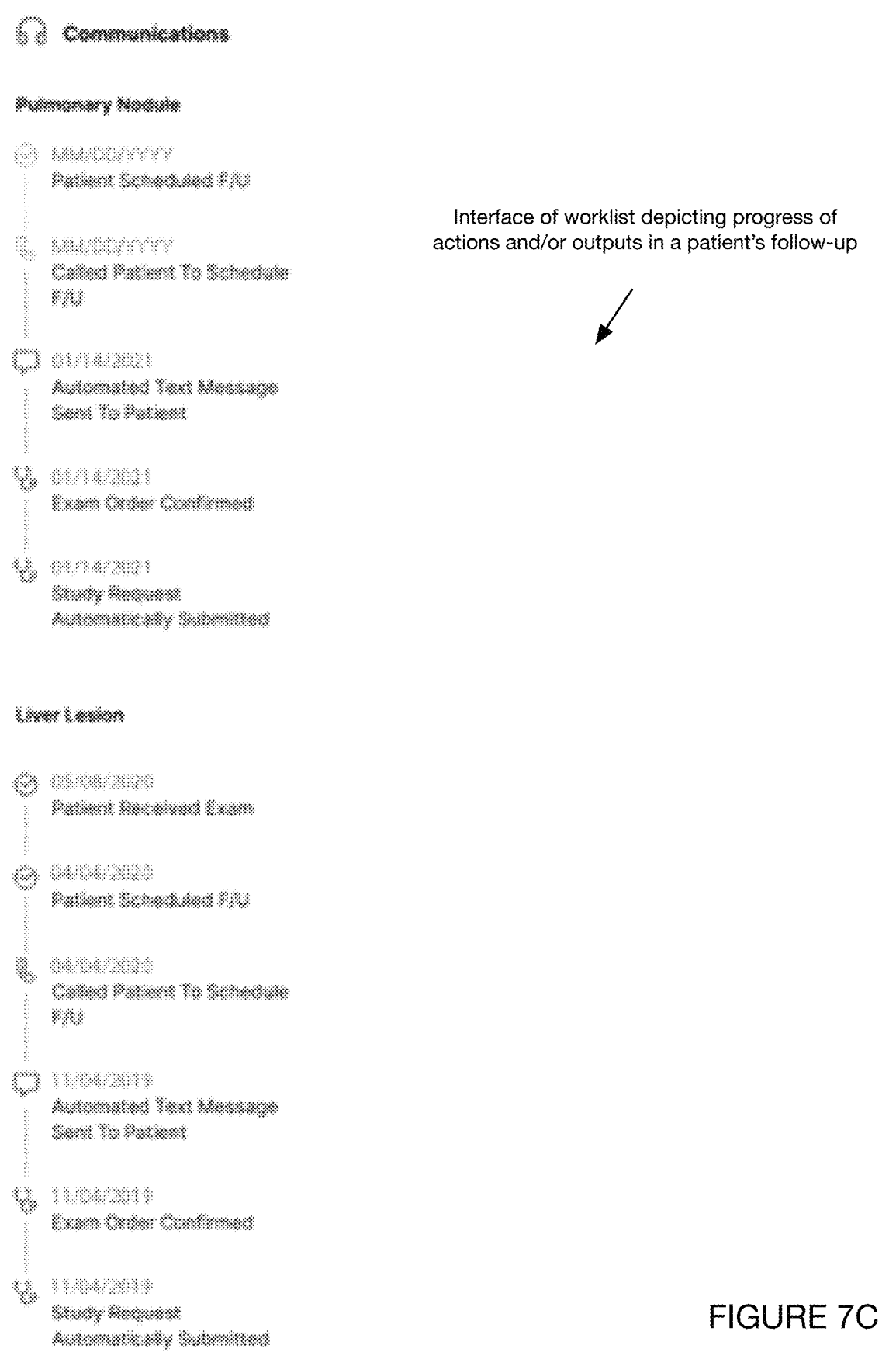
Figure 7D:
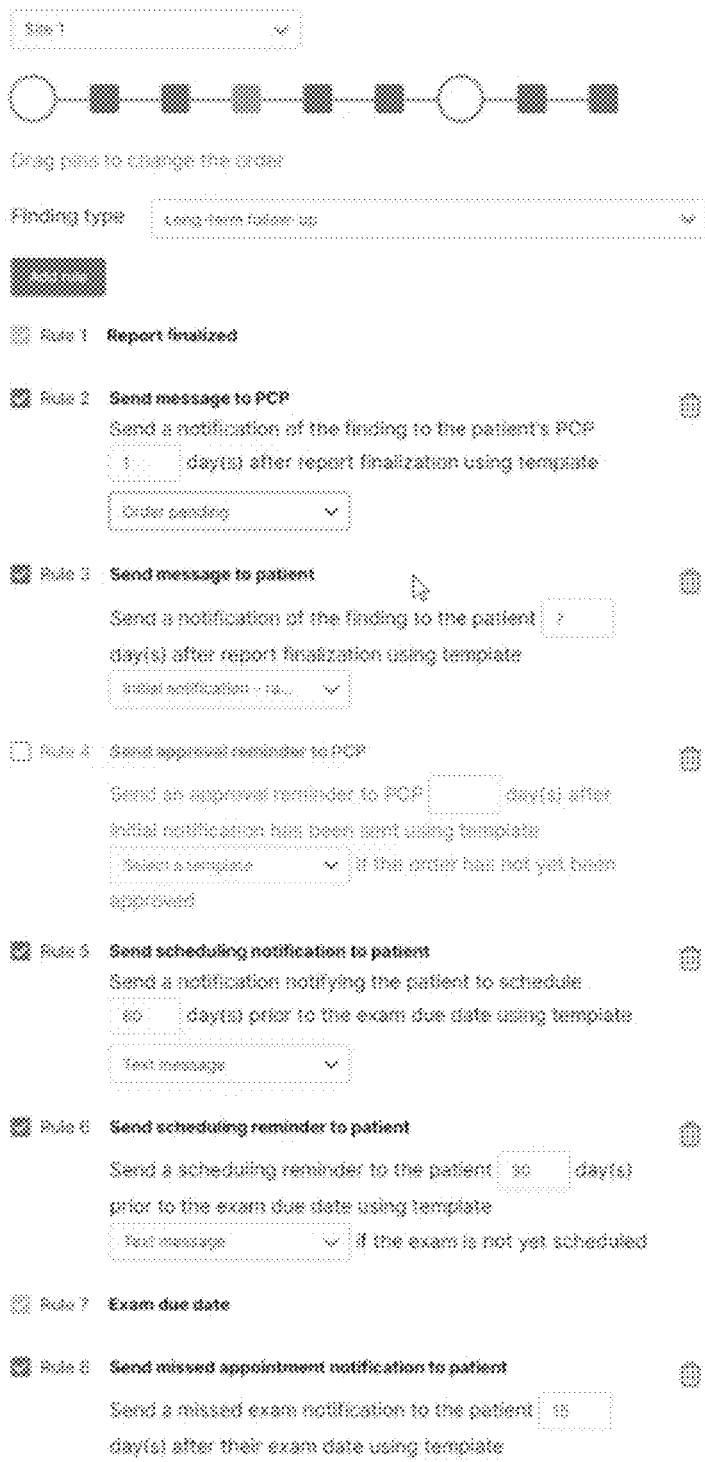
Figure 7E:
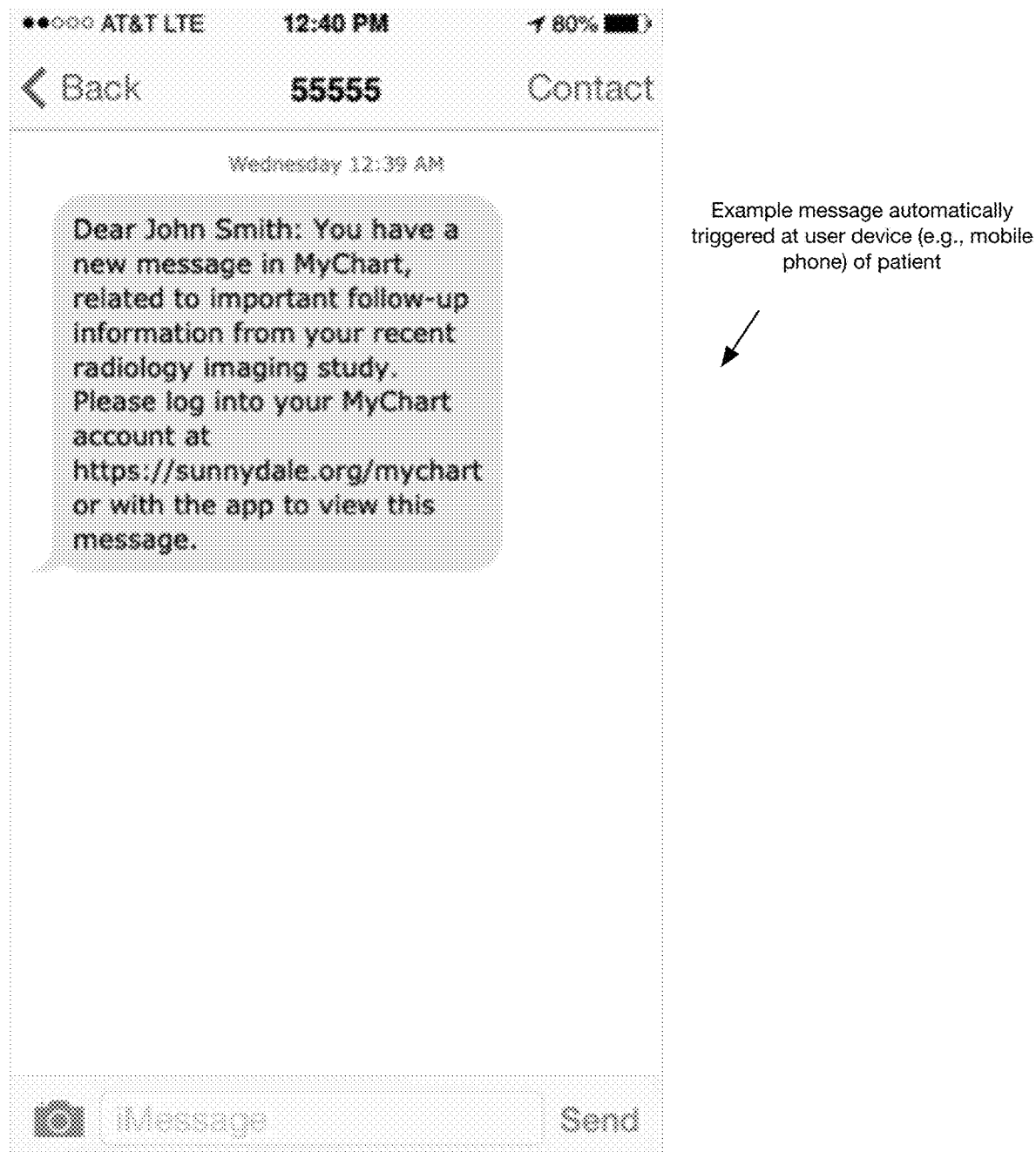

In a third variation (e.g., as shown in FIG. 7A), S400 includes facilitating the assignment of a PCP to a patient upon determining that the patient does not currently have a PCP. This can include, for instance, any or all of: compiling (e.g., automatically compiling) and sending a list of PCP options (e.g., based on their availability, based on their proximity to the patient, based on the patient's insurance, etc.) to the patient; contacting the recommended PCP(s) and notifying them of the patient; referring the patient to the PCP; and/or triggering any other actions.

S400 can optionally include scheduling any or all of the follow-up recommendations, such as automatically scheduling any or all of: follow-up imaging; one or more appointments (e.g., with a primary care physician, with a specialist, etc.) and/or specialist consultations; laboratory testing; a procedure; emergency intervention; and/or any other suitable follow-up. Scheduling the follow-up can optionally include interfacing with one or more systems and/or interfaces, such as any or all of: a healthcare facility scheduling system; the calendar and/or availability of the patient; the calendar and/or availability of a physician; the calendar and/or availability of a radiologist and/or laboratory technician; and/or any other systems.

At least a portion of the actions and/or outputs are preferably performed and/or triggered automatically (e.g., without user input), but any or all can additionally or alternatively be partially or fully performed manually (e.g., by a user).

In some variations, for instance, S400 can include automatically scheduling follow-up imaging at a predetermined later time point according to the follow-up recommendation.

S400 can optionally include organizing any or all patients and/or reports, which can function to enable one or more users to view, manage, and/or prioritize any or all of the actions and/or outputs associated with a follow-up recommendation. The user preferably includes one or more users involved in a case and/or patient management capacity, such as, but not limited to: a case manager (e.g., for a radiology department, radiology group, healthcare facility, department, etc.), facilitator, nurse navigator, and/or any other managers associated with a healthcare facility, radiology group, and/or any other entities. Additionally or alternatively, the information can be accessible by (e.g., continuously accessible by, selectively accessibly by, accessible by in an event of a particular action/trigger, etc.): patients, radiologists, physicians (e.g., PCPs), all users, others users, and/or any combination of users.

In a preferred set of variations, for instance, S400 includes automatically populating, managing, and organizing a set of one or more worklists accessible by one or more users for tracking and managing the actions and/or outputs for patient follow-up. In a set of specific examples (e.g., as shown in FIGS. 7A-7E), a follow-up worklist is created and populated which enables users to view, track, and manage the actions and outputs specified by the follow-up recommendations determined in S300.

The worklists (and/or any other interfaces) can optionally receive information regarding events that happen outside of this system and/or facility (e.g., from RIS, EHR, etc.) in order to automatically update the status (e.g., if imaging happens) of follow-up actions. Additionally or alternatively, historical information associated with the patient (e.g., findings and/or follow-up recommendations from prior studies) can be received and used in determining and/or managing the outputs and/or actions.

The follow-up worklist can optionally be split and/or configured to be viewed into multiple worklists. In some variations (e.g., as shown in FIG. 6), for instance, in an event that a follow-up recommendation is incomplete and/or missing, the patient and associated radiology report can be populated within a secondary worklist, which can function to alert the manager or other user that a follow-up recommendation is missing (e.g., to trigger the report being sent back to the radiologist for completion, for completion by the manager or other user, for validation by the manager or other user of an auto-generated recommendation, etc.), whereas complete radiology reports populate a primary worklist.

The worklists and/or other interfaces can optionally be sorted and/or filtered (e.g., as shown in FIGS. 7A-7E), which can function to: help users prioritize which patients to follow up with (e.g., manually); trigger supplemental actions and/or outputs (e.g., in response to the patient not performing an action within a predetermined threshold of time); determine (e.g., quickly determine) how overdue an action might be; ensure that the follow-up recommendations are performed and/or complied with; prevent patients from being forgotten and/or ignored; and/or can perform any other functions. In a first set of examples, the patients in one or more worklists are sorted according to one or more temporal parameters (e.g., due date, number of days a follow-up action is overdue, etc.) associated with their follow-up recommendations. Additionally or alternatively, any or all of the temporal parameters can be used to determine a progress metric (e.g., according to a predetermined equation, aggregated in a weighted fashion, etc.) associated with the patient's progress in completing his or her triggered actions. Further additionally or alternatively, the progress metric can take into account any or all of: a number of actions/outputs which have been completed; an average time in which the actions/outputs are completed; a number of days in which an action/output has been completed or not completed relative to a predetermined time limit associated with the action; and/or any other information. In a second set of examples, the patients are additionally or alternatively sorted according to the particular finding detected in their study, such as based on a severity metric and/or urgency metric associated with the particular finding (e.g., as determined with a lookup table, as determined with a weighted algorithm, etc.). In a third set of specific examples, the patients are additionally or alternatively sorted based on demographic and/or historical information associated with the patient, such as: other comorbidities associated with the patient, a risk metric determined based on demographic information and/or historical health information of the patient, a progression of the finding (e.g., based on prior studies); and/or any other information. In a particular specific example, a risk metric is calculated based on any or all of this information, where the patients are sorted to indicate the highest risk patients first.

S400 can optionally include tracking any or all of the follow-up recommendations, which can function to ensure that follow-up is performed, monitor incidental findings which do not have current specific follow-up, determine when follow-up no longer needs to be continued (e.g., in an event that the incidental finding is improving and/or no longer present), and/or can perform any other functions.

The tracking can include, for instance, automatically sending notifications to any or all of the entities described above, such as at a predetermined frequency (e.g., every month, every 3 months, every 6 months, every year, etc.) until the follow-up is performed. Additionally or alternatively, tracking can include routinely checking the patient's medical information (e.g., medical files, PACS, etc.) to see if the follow-up has been performed.

In a set of specific examples, the tracking includes tracking the same incidental finding and/or or group of incidental findings in the same body system across multiple follow-up studies and/or other actions for any predetermined and/or dynamically determined time period (e.g., over the course of multiple years, until a predetermined number of years has passed, etc.)

S400 can additionally or alternatively include any or all of: checking to see if follow-up is performed; verifying that the follow-up is performed; and verifying that the follow-up which was performed satisfies the associated recommendation. These can individually and/or collectively function to effectively "close the loop" on the patient and/or study and/or set of follow-up recommendations (e.g., to trigger removal of the patient from a set of worklists, to cease sending messages and/or reminders to one or more users, etc.). In preferred variations, these processes are performed at least partially automatically (e.g., all fully automatically), but can additionally or alternatively be performed at least partially manually (e.g., with user input), and/or any combination of automatically and manually.

In a first set of variations, for instance, S400 includes detecting whether or not an action performed by or for the patient satisfies the follow-up recommendation and/or a set of requirements associated with the set of follow-up recommendations. These can include any or all of: actions which are associated with (e.g., triggered based on) a particular finding and/or follow-up recommendation (e.g., an imaging study automatically scheduled in response to a particular follow-up recommendation; actions which are performed independently of a finding and/or follow-up recommendation (e.g., routinely performed, ordered for another reason, etc.); any combination; and/or any other actions.

In some examples, for instance, whenever additional studies are done for the patient (e.g., even if not ordered specifically to follow up that incidental finding), S400 can include detecting (e.g., automatically detecting) whether or not the study satisfies any or all requirements associated with follow-up for the patient (e.g., pending/outstanding follow-up requirements) and optionally closing out the follow-up recommendation in response to satisfaction of any or all criteria. This preferably applies to all studies or other actions associated with the patient, such as, but not limited to: studies performed at other healthcare facilities (e.g., facilities outside of the patient's catchment area), studies performed for other reasons, and/or any other studies. Examples of these requirements can include, but are not limited to, any or all of: detecting that the study imaged a required area; detecting that the same incidental finding was mentioned again in that study's associated report; detecting that the study falls within a recommended timeframe (e.g., with a customizable grace period, without a customizable grace period, etc.); and/or detecting any other information/ features associated with the performed action. Additionally or alternatively, S400 can include closing the loop (e.g., cancelling further follow-up actions, removing from a worklist, etc.) on a patient upon determining and/or receiving an input (e.g., from the patient's provider) that indicates that any or all follow-up actions (e.g., further study) is not clinically necessary and/or recommended (e.g., due to the patient's existing comorbidities, due to the patient's advanced age, etc.).

Additionally or alternatively, S400 can include any other suitable processes, such as automatically creating one or flags (e.g., in the radiology report, in notes for a physician, in a discharge order, etc.), and/or any other suitable processes.

4.4 Method—Variations

Figure 4:
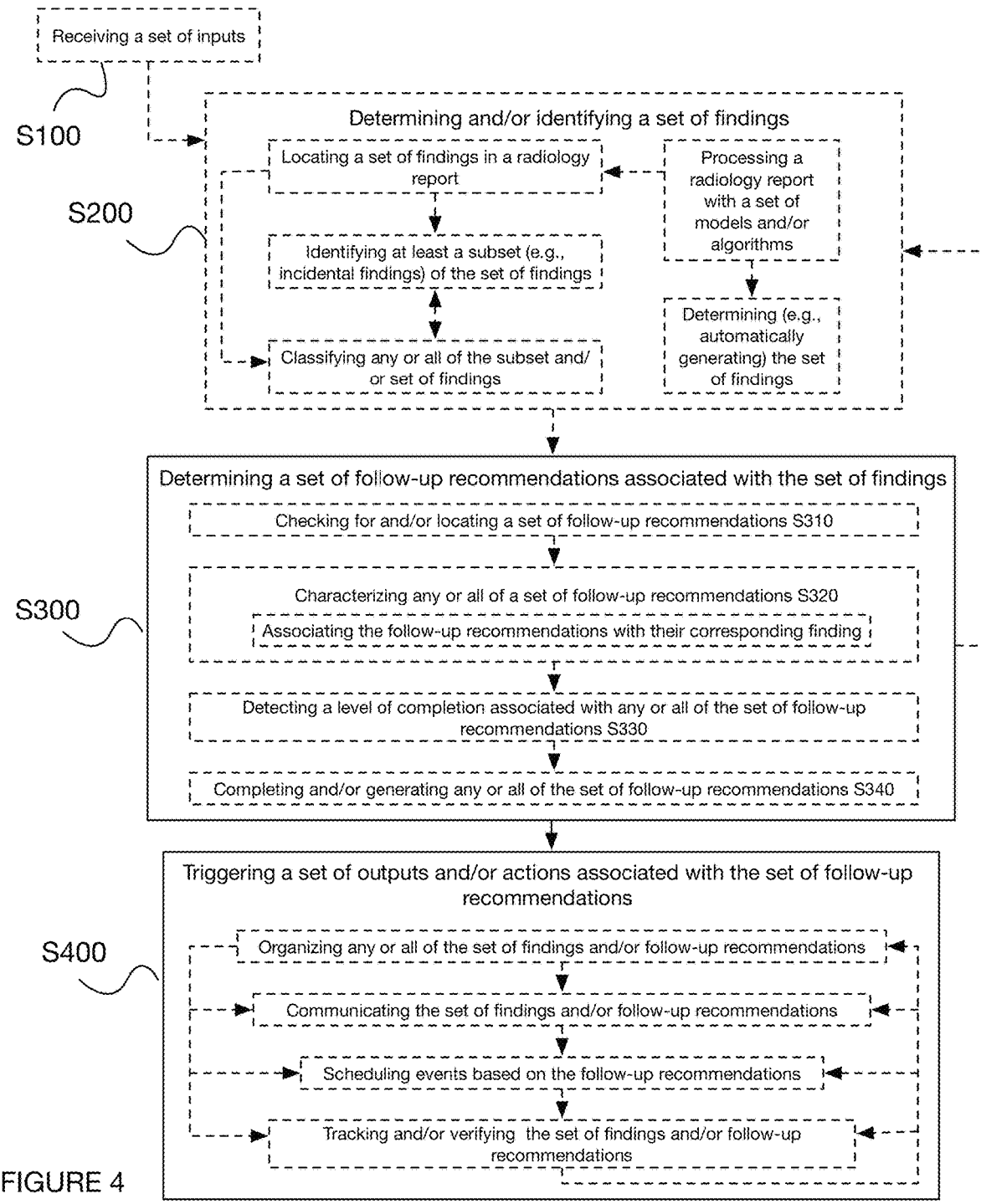
FIG. 4 depicts a variation of the method for identifying and tracking radiology findings.

In a first variation of the method 200 (e.g., as shown in FIG. 4), the method 200 includes any or all of: processing a radiology report to locate a findings section and/or set of findings; evaluating (e.g., with a set of trained models and/or algorithms, with natural language processing, with a set of lookup tables, with a decision tree, with a set of trained classifiers, etc.) the located findings to classify any or all of the set of findings; identifying a set of incidental findings based on the classification(s); locating a set of follow-up recommendations in the radiology report; associating each of the set of incidental findings with one or more follow-up recommendations; in an event that any of the follow-up recommendations for an incidental finding are incomplete and/or missing, triggering an action (e.g., auto-completing the recommendation, automatically generating the recommendation, flagging/providing the report to a user for completion, etc.); determining a set of actions and/or outputs configured to facilitate and ensure performance of the follow-up recommendations; and triggering the set of outputs and/or actions.

In a first set of specific examples, the method 200 includes any or all of: processing the radiology report with a set of trained models (e.g., trained machine learning models, trained deep learning models, trained neural networks, natural language processing models, etc.) to determine/detect any or all of: a findings section and/or a set of findings in the radiology report (e.g., based on a predetermined set of keywords associated with particular findings and/or findings collectively); a set of follow-up recommendations; an association between any or all of the set of findings and any or all of the set of recommendations (e.g., associating each of the set of incidental findings with its corresponding follow-up recommendation(s)); a missing and/or incomplete follow-up recommendation; an optimal output and/or action to trigger (e.g., as determined with a predictive model); an optimal time and/or recipient at/to which trigger the output and/or action; and/or any other determinations or detections.

In a second set of examples, additional or alternative to the first, checking for the set of findings is performed prior to checking for and/or determining the set of follow-up recommendations.

In a third set of examples, additional or alternative to those described above, checking for the set of findings is performed after checking for and/or locating the set of follow-up recommendations.

In a fourth set of examples, additional or alternative to those described above, checking for the set of findings is performed in parallel with checking for and/or locating and/or generating the set of follow-up recommendations.

In a fifth set of examples, additional or alternative to those described above, the method 200 is performed in absence of one or both of: checking for the set of findings and checking for (and/or locating and/or generating) the set of follow-up recommendations.

In a second variation of the method 200 (e.g., as shown in FIG. 4), the method 200 includes: processing a set of images with a set of models and/or algorithms (e.g., trained models) to automatically detect a set of incidental findings associated with the images (and optionally any other findings); determining (e.g., automatically generating) a set of follow-up recommendations (e.g., with a set of models and/or algorithms) associated with any or all of set of findings; inserting the follow-up recommendations into a radiology report (e.g., new radiology report, existing radiology report which is partially finished, etc.); determining a set of actions and/or outputs configured to facilitate and ensure performance of the follow-up recommendations; and triggering the set of outputs and/or actions. The method 200 can optionally additionally or alternatively include any or all of: receiving a radiology report (e.g., manually generated radiology report, automatically generated radiology report, partially finished radiology report, etc.); locating an existing set of findings within the radiology report; and comparing the set of findings (e.g., incidental findings) in the radiology report with those automatically generated (e.g., to detect if any incidental findings are missing in the report).

In a third variation of the method 200 (e.g., as shown in FIG. 4), the method 200 includes: processing a radiology report to locate a set of follow-up recommendations in the radiology report; processing the set of follow-up recommendations to detect a completion associated with each of the set of follow-up recommendations; and in response to detecting that any or all of the follow-up recommendations are incomplete, performing at least one of assigning the report and/or associated study and/or patient to a secondary dataset (e.g., secondary worklist) and automatically generating and inserting a missing portion of the follow-up recommendation into the radiology report.

In a first set of examples, the method 200 includes referencing a predetermined lookup table to generate and/or complete the set of follow-up recommendations. The predetermined lookup table preferably includes, is generated based on, and/or is generated in accordance with a set of radiology consensus guidelines, radiology best practices, a set of preferences (e.g., of the radiology group, of the patient, of the patient's primary care physician, etc.), and/or any other information.

In a second set of examples, the method 200 generates and/or completes a set of follow-up recommendations with a set of models and/or algorithms (e.g., trained machine learning models, neural networks, etc.).

In a third set of examples, additional or alternative to those described above, in response to detecting that a follow-up recommendation is missing and/or incomplete, the method 200 automatically triggers an assignment of the study to a secondary worklist associated with a user, such that the user can complete and/or flag the study for completion (e.g., by the radiologist who generated the report).

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-public transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-public transitory computer readable media, or any suitable device. The computer-executable component can include a computing system and/or processing system (e.g., including one or more collocated or distributed, remote or local processors) connected to the non-public transitory computer-readable medium, such as CPUs, GPUs, TPUS, microprocessors, or ASICs, but the instructions can alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

We claim:

1. A method for computer-assisted implementation of a set of follow-up recommendations associated with a set of patients, the method comprising:
   for each patient of the set of patients:
      receiving a radiology report associated with the patient;
      automatically processing the radiology report, comprising:
         determining a set of incidental findings in the radiology report, wherein determining the set of incidental findings comprises:
            processing the radiology report with a first set of trained neural network models to detect a set of findings, the first set of trained neural network models comprising a first multi-transformer model configured to implement parallelization;
            processing the set of findings with a first set of rule-based logic to determine a first set of features, wherein the first set of rule-based logic is configured to determine a context associated with the detected set of findings, wherein determining the context comprises checking for inclusion of negation words proximal to the set of findings;
            determining the set of incidental findings based on the first set of features;
         determining a set of follow-up recommendations associated with the set of incidental findings in the radiology report, wherein determining the set of follow-up recommendations comprises:
            processing the radiology report with a second set of trained neural network models to locate a set of recommendation candidate sentences, the second set of trained neural network models comprising a second multi-transformer model configured to implement parallelization;
            processing each of the set of recommendation candidate sentences with a second set of rule-based logic to determine:
               a second set of features for the set of recommendation candidate sentences; and
               a level of completion for each of the set of recommendation candidate sentences;
            determining the set of follow-up recommendations based on at least one of the second set of features and the levels of completion;
   for the set of patients, initiating a set of follow-up actions in response to automatically processing the radiology report, wherein automatically initiating the set of follow-up actions comprises, automatically:
      scheduling a set of follow-up imaging processes for a first subset of the set of patients;
      messaging a set of primary care physicians associated with a second subset of the set of patients; and
      upon detecting that each patient of a third subset of the set of patients does not have a primary care physician, initiating the assignment of a second set of primary care physicians to the third subset of patients; and
   automatically populating a set of worklists based on the set of follow-up actions.

2. The method of claim 1, further comprising comparing the set of incidental findings with the set of follow-up recommendations to check for a set of missing follow-up recommendations.

3. The method of claim 2, wherein automatically populating the set of worklists comprises:
- in response to determining that there are no missing follow-up recommendations for a patient of the set of patients, triggering an assignment of the patient to a first worklist of the set of worklists;
- in response to determining at least one of: the presence of at least one missing follow-up recommendation and a level of completion below a threshold associated with a follow-up recommendation, performing at least one of:
  - triggering an assignment of the patient to a second worklist; and
  - automatically adding supplemental text to the radiology report.

4. The method of claim 1, wherein processing the findings section further comprises evaluating a decision tree based on the first set of features, wherein determining the set of incidental findings comprises categorizing a portion of the set of findings as the set of incidental findings based on evaluating the decision tree.

5. The method of claim 4, wherein categorizing the portion further comprises assigning a particular type of incidental finding to the findings text.

6. The method of claim 1, wherein the first set of features comprises a size measurement.

7. The method of claim 1, wherein the set of findings is detected based at least in part on a predetermined set of pathology keywords.

8. The method of claim 1, wherein automatically organizing each of the first and second worklists comprises sorting the patients based on a progress metric associated with the follow-up recommendation.

9. The method of claim 8, wherein the set of patients is further sorted based on a type associated with each of the set of incidental findings.

10. The method of claim 9, wherein the set of patients is further sorted based on risk metric calculated for the patient, wherein the risk metric is calculated based on at least one of: demographic information associated with the patient and a medical history associated with the patient.

11. The method of claim 1, wherein the method is performed absent of radiologist input.

12. The method of claim 1, further comprising, in response to detecting that a follow-up recommendation of the set of follow-up recommendations has a completion level below a predetermined threshold, automatically adding supplemental text to the radiology report.

13. The method of claim 12, further comprising determining the supplemental text, wherein determining the supplemental text comprises referencing a lookup table.

14. The method of claim 13, wherein the lookup table is determined based on a set of radiology consensus guidelines.

15. The method of claim 1, wherein each of the first and second set of trained neural network models comprises a neural network.

16. The method of claim 1, wherein determining the set of findings comprises locating a predetermined findings section of the radiology report.

17. The method of claim 1, wherein the first and second multi-transformer models are not required to process data in the radiology report in order.

* * * * *